United States Patent [19]
Koops et al.

[11] Patent Number: 6,057,494
[45] Date of Patent: May 2, 2000

[54] DNA SEQUENCES ENCODING CARBOHYDRATE POLYMER SYNTHESIZING ENZYMES AND METHOD FOR PRODUCING TRANSGENIC PLANTS

[75] Inventors: Andries Jurriaan Koops; Ingrid Maria van der Meer; Arjen Johannus Van Tunen, all of Wageningen, Netherlands

[73] Assignee: Centrum Voor Plantenveredelings-En Reproduktieonderzoek, Wageningen, Netherlands

[21] Appl. No.: 08/860,091
[22] PCT Filed: Jan. 8, 1996
[86] PCT No.: PCT/NL96/00012
   § 371 Date: Aug. 25, 1997
   § 102(e) Date: Aug. 25, 1997
[87] PCT Pub. No.: WO96/21023
   PCT Pub. Date: Jul. 11, 1996

[30] Foreign Application Priority Data

Jan. 6, 1995 [EP] European Pat. Off. ............... 95200015
Mar. 27, 1995 [EP] European Pat. Off. ............... 95200762

[51] Int. Cl.[7] .......................... C12N 15/82; C12N 15/29; C12N 15/54; C12P 19/04; A01H 5/00
[52] U.S. Cl. ......................... 800/284; 800/286; 800/298; 435/101; 435/419; 435/468; 435/471; 435/193; 536/23.6; 536/24.5
[58] Field of Search .................................. 536/23.6, 24.5; 800/284, 286, 298; 435/101, 193, 419, 468, 471

[56] References Cited

FOREIGN PATENT DOCUMENTS 8912386 12/1989 WIPO .
9414970 7/1994 WIPO .
9601904 1/1996 WIPO .

OTHER PUBLICATIONS

Stratagene Instruction Manual: UniZAP™ Library, Jan. 19, 1994, pp. 1–10.
Sambrook et al. Molecular Cloning: A Laboratory Manual, Second Edition, Cold Spring Harbor Lab. Press, pp. 8.46–8.47, 1989.
Hellwege et al. Plant Journal 12(5):1057–1065, 1997.
Bournay et al. Nucl. Acids Res. 24(12):2347–2351, 1996.
Kossmann et al. Progress in Biotechnol. 10:271–278, 1995.
Angenent et al. "Purification and Properties of Sucrose Fructosyltransferases from Barley Leaves and Onion Seeds" by Angenent, G.C., et al., *Insulin and Insulin–containing Crops*, 1993, pp. 173–184, Fuchs, A., ed.
Praznik, W., et al., "Isolation and Characterization of Sucrose:Sucrose $1^F$–β–D– Fructosyltransferase from Tubers of *Helianthus tuberosus* L." Agricultural Biol. Chem., vol. 54, No. 9, 1990, pp. 2429–2431.
Lüscher, M., et al., "Purification and characterization of fructan: fructan fructosyltransferase from Jerusalem artichoke (*Helianthus tuberosus* L.)", *New Phytol*, vol. 123, 1993, pp. 717–724.
Koops, A., et al., "Purification and characterization of the enzymes of fructan biosynthesis in tubers of *Helianthus tuberosus* "Colombia" I. Fructan:fructan fructosyltransferase" *Journal of Experimental Botany*, vol. 45, No. 280, Nov. 1994, pp. 1623–1631.

*Primary Examiner*—David T. Fox
*Attorney, Agent, or Firm*—Ladas & Parry

[57] ABSTRACT

A DNA fragment is disclosed having a nucleotide sequence SEQ ID NO. 1 as shown in FIG. 4A or a homologous sequence having a similarity of at least 70% encoding 1-sucrose:sucrose fructosyltransferase. Another DNA fragment that is disclosed is a DNA fragment having a nucleotide sequence SEQ ID NO. 3 as shown in FIG. 4B or a homologous sequence having a similarity of at least 70% encoding 1-fructan:fructan fructosyltransferase. This invention also discloses a recombinant DNA comprising one or more of said DNA fragments, or comprising said DNA fragment(s) in the inverted orientation. Transformed organisms showing a modified fructan profile can be produced using said fragments.

26 Claims, 12 Drawing Sheets

A. SEQ ID. NO. 1.

FIG. 4A

```
GGCACGAGAAAAAACCCTCCCTCAGGCCACCACATGATGGCTTCATCCACCACCACCACC  60
                                   M  M  A  S  T  T  T  T
CCTCTCATTCTCCATGATGACCCTGAAAACCTCCCAGAACTCACCGGTTCTCCGACAACT  120
 P  L  I  L  H  D  D  P  E  N  L  P  E  L  T  G  S  P  T  T
CGTCGTCTATCCATCGCAAAAGTGCTTTCGGGGATCCTTGTTTCGGTTCTGGTTATAGGT  180
 R  R  L  S  I  A  K  V  L  S  G  I  L  V  S  L  V  I  G
GCTCTTGTTGCTTTAATCAACAACCAAACATATGAATCCCCCTCGGCCACCACATTCGTA  240
 A  L  V  A  L  I  N  N  Q  T  Y  E  S  P  S  A  T  T  F  V
ACTCAGTTGCCAAATATTGATCTGAAGCGGGTTCCAGGAAAGTTGGATTCGAGTGCTGAG  300
 T  Q  L  P  N  I  D  L  K  R  V  P  G  K  L  D  S  S  A  E
GTTGAATGGCAACGATCCACTTATCATTTTCAACCCGACAAAAATTTCATTAGCGATCCT  360
 V  E  W  Q  R  S  T  Y  H  F  Q  P  D  K  N  F  I  S  D  P
GATGGCCCAATGTATCACATGGGATGGTATCATCTATTTTATCAGTACAACCCTCAATCT  420
 D  G  P  M  Y  H  M  G  W  Y  H  L  F  Y  Q  Y  N  P  Q  S
GCCATCTGGGGCAACATCACATGGGGCCACTCGGTATCGAAAGACATGATCAACTGGTTC  480
 A  I  W  G  N  I  T  W  G  H  S  V  S  K  D  M  I  N  W  F
CATCTCCCTTTCGCCATGGTTCCTGACCATTGGTACGACATCGAAGGTGTCATGACGGGT  540
 H  L  P  F  A  M  V  P  D  H  W  Y  D  I  E  G  V  M  T  G
TCGGCTACAGTCCTCCCTAATGGTCAAATCATCATGCTTTACTCGGGCAACGCGTATGAT  600
 S  A  T  V  L  P  N  G  Q  I  I  M  L  Y  S  G  N  A  Y  D
CTCTCCCAAGTACAATGCTTGGCGTACGCTGTCAACTCGTCGGATCCACTTCTTATAGAG  660
 L  S  Q  V  Q  C  L  A  Y  A  V  N  S  S  D  P  L  L  I  E
TGGAAAAAATATGAAGGTAACCCTGTCTTACTCCCACCACCAGGAGTAGGCTACAAGGAC  720
 W  K  K  Y  E  G  N  P  V  L  L  P  P  P  G  V  G  Y  K  D
TTTCGGGACCCATCCACATTGTGGTCGGGCCCTGATGGTGAATATAGAATGGTAATGGGG  780
 F  R  D  P  S  T  L  W  S  G  P  D  G  E  Y  R  M  V  M  G
TCCAAGCACAACGAGACTATTGGCTGTGCTTTGATTTACCATACCACTAATTTTACGCAT  840
 S  K  H  N  E  T  I  G  C  A  L  I  Y  H  T  T  N  F  T  H
TTTGAATTGAAAGAGGAGGTGCTTCATGCAGTCCCACATACTGGTATGTGGGAATGTGTT  900
 F  E  L  K  E  E  V  L  H  A  V  P  H  T  G  M  W  E  C  V
GATCTTTACCCGGTGTCCACCGTACACACAAACGGGCTGGACATGGTGGATAACGGGCCA  960
 D  L  Y  P  V  S  T  V  H  T  N  G  L  D  M  V  D  N  G  P
AATGTTAAGTACGTGTTGAAACAAAGTGGGGATGAAGATCGCCATGATTGGTATGCAATT  1020
 N  V  K  Y  V  L  K  Q  S  G  D  E  D  R  H  D  W  Y  A  I
GGAAGTTACGATATAGTGAATGATAAGTGGTACCCAGATGACCCGGAAAATGATGTGGGT  1080
 G  S  Y  D  I  V  N  D  K  W  Y  P  D  D  P  E  N  D  V  G
ATCGGATTAAGATATGATTTTGGAAAATTTTATGCGTCCAAGACGTTTTATGACCAACAT  1140
 I  G  L  R  Y  D  F  G  K  F  Y  A  S  K  T  F  Y  D  Q  H
AAGAAGAGGAGAGTCCTTTGGGGCTATGTTGGAGAAACCGATCCCCAAAAGTATGACCTT  1200
 K  K  R  R  V  L  W  G  Y  V  G  E  T  D  P  Q  K  Y  D  L
TCAAAGGGATGGGCTAACATTTTGAATATTCCAAGGACCGTCGTTTTGGACCTCGAAACT  1260
 S  K  G  W  A  N  I  L  N  I  P  R  T  V  V  L  D  L  E  T
```

FIG. 4A (cont.)

```
AAAACCAATTTGATTCAATGGCCAATCGAGGAAACCGAAAACCTTAGGTCGAAAAAGTAT 1320
  K   T  N  L  I  Q  W  P  I  E  E  T  E  N  L  R  S  K  K  Y
GATGAATTTAAAGACGTCGAGCTTCGACCCGGGGCACTCGTTCCCCTTGAGATAGGCACA 1380
  D   E  F  K  D  V  E  L  R  P  G  A  L  V  P  L  E  I  G  T
GCCACACAGTTGGATATAGTTGCGACATTCGAAATCGACCAAAAGATGTTGGAATCAACG 1460
  A   T  Q  L  D  I  V  A  T  F  E  I  D  Q  K  M  L  E  S  T
CTAGAGGCCGATGTTCTATTCAATTGCACGACTAGTGAAGGCTCGGTTGCAAGGAGTGTG 1500
  L   E  A  D  V  L  F  N  C  T  T  S  E  G  S  V  A  R  S  V
TTGGGACCGTTTGGTGTGGTGGTTCTAGCCGATGCCCAGCGCTCCGAACAACTTCCTGTA 1560
  L   G  P  F  G  V  V  V  L  A  D  A  Q  R  S  E  Q  L  P  V
TACTTCTATATCGCAAAAGATATTGATGGAACCTCACGAACTTATTTTTGTGCCGACGAA 1620
  Y   F  Y  I  A  K  D  I  D  G  T  S  R  T  Y  F  C  A  D  E
ACAAGATCATCCAAGGATGTAAGCGTAGGGAAATGGGTGTACGGAAGCAGTGTTCCTGTC 1680
  T   R  S  S  K  D  V  S  V  G  K  W  V  Y  G  S  S  V  P  V
CTCCCAGGCGAAAAGTACAATATGAGGTTATTGGTGGATCATTCGATAGTAGAGGGATTT 1740
  L   P  G  E  K  Y  N  M  R  L  L  V  D  H  S  I  V  E  G  F
GCACAAAACGGGAGAACCGTGGTGACATCAAGAGTGTATCCAACAAAGGCGATCTACAAC 1800
  A   Q  N  G  R  T  V  V  T  S  R  V  Y  P  T  K  A  I  Y  N
GCTGCGAAGGTGTTTTTGTTCAACAACGCGACTGGAATCAGTGTGAAGGCGTCGATCAAG 1860
  A   A  K  V  F  L  F  N  N  A  T  G  I  S  V  K  A  S  I  K
ATCTGGAAGATGGGGGAAGCAGAACTCAATCCTTTCCCTCTTCCTGGGTGGACTTTCGAA 1920
  I   W  K  M  G  E  A  E  L  N  P  F  P  L  G  W  T  F  E
CTTTGATGGTTATATTTTGGACCCTATATATGTGTTATTATCATGATGGTTATATTTTGG 1980
  L
ACCCTATATATGTGTTATTATCATGAAGCATAAGTTTGGACTGGAGGGGGTATTATTGTA 2040
ATTTTATATGCATGTTCTATTACTTGTGAGGTTATAGTATGTAATTAAATTATTATATAC 2100
TATATCAATTTCTAAT                                             2116
```

B. SEQ ID. NO. 2.

FIG. 4B

```
GGGACGAGTACCAGTCCAGTCAGTCACCATGCAAACCCCTGAACCCTTTACAGACCTTGA 60
                                 M  Q  T  P  E  P  F  T  D  L  E
ACATGAACCCCACACACCCCTACTGGACCACCACCACAACCCACCACCACAAACCACCAC 120
  H  E  P  H  T  P  L  L  D  H  H  H  N  P  P  P  Q  T  T
AAAACCTTTGTTCACCAGGGTTGTGTCCGGTGTCACCTTTGTTTTATTCTTCTTTGGTTT 180
  K  P  L  F  T  R  V  V  S  G  V  T  F  V  L  F  F  G  F
CGCTATCGTATTCATTGTTCTCAACCAACAGAATTCTTCTGTTCGTATCGTCACCAATTC 240
  A  I  V  F  I  V  L  N  Q  Q  N  S  S  V  R  I  V  T  N  S
GGAGAAATCTTTTATAAGGTATTCGCAGACCGATCGCTTGTCGTGGGAACGGACCGCTTT 300
  E  K  S  F  I  R  Y  S  Q  T  D  R  L  S  W  E  R  T  A  F
TCATTTTCAGCCTGCCAAGAATTTTATTTACGATCCAGATGGTCAGTTGTTTCACATGGG 360
  H  F  Q  P  A  K  N  F  I  Y  D  P  D  G  Q  L  F  H  M  G
CTGGTACCATATGTTCTATCAATACAACCCATACGCACCGGTTTGGGGCAATATGTCATG 420
  W  Y  H  M  F  Y  Q  Y  N  P  Y  A  P  V  W  G  N  M  S  W
GGGTCACTCAGTGTCCAAAGACATGATCAACTGGTACGAGCTGCCAGTCGCTATGGTCCC 480
  G  H  S  V  S  K  D  M  I  N  W  Y  E  L  P  V  A  M  V  P
GACCGAATGGTATGATATCGAGGGCGTCTTATCCGGGTCTACCACGGTCCTTCCAAACGG 540
  T  E  W  Y  D  I  E  G  V  L  S  G  S  T  T  V  L  P  N  G
TCAGATCTTTGCATTGTATACTGGGAACGCTAATGATTTTTCCCAATTACAATGCAAAGC 600
  Q  I  F  A  L  Y  T  G  N  A  N  D  F  S  Q  L  Q  C  K  A
TGTACCCGTAAACTTATCTGACCCGCTTCTTATTGAGTGGGTCAAGTATGAGGATAACCC 660
  V  P  V  N  L  S  D  P  L  L  I  E  W  V  K  Y  E  D  N  P
AATCCTGTACACTCCACCAGGGATTGGGTTAAAGGACTATCGGGACCCGTCAACAGTCTG 720
  I  L  Y  T  P  P  G  I  G  L  K  D  Y  R  D  P  S  T  V  W
GACAGGTCCCGATGGAAAGCATAGGATGATCATGGGAACTAAACGTGGCAATACAGGCAT 780
  T  G  P  D  G  K  H  R  M  I  M  G  T  K  R  G  N  T  G  M
GGTACTTGTTTACTATACCACTGATTACACGAACTACGAGTTGTTGGATGAGCCGTTGCA 840
  V  L  V  Y  Y  T  T  D  Y  T  N  Y  E  L  L  D  E  P  L  H
CTCTGTTCCCAACACCGATATGTGGGAATGCGTCGACTTTTACCCGGTTTCGTTAACCAA 900
  S  V  P  N  T  D  M  W  E  C  V  D  F  Y  P  V  S  L  T  N
TGATAGTGCACTTGATATGGCGGCCTATGGGTCGGGTATCAAACACGTTATTAAAGAAAG 960
  D  S  A  L  D  M  A  A  Y  G  S  G  I  K  H  V  I  K  E  S
TTGGGAGGGACATGGAATGGATTGGTATTCAATCGGGACATATGACGCGATAAATGATAA 1020
  W  E  G  H  G  M  D  W  Y  S  I  G  T  Y  D  A  I  N  D  K
ATGGACTCCCGATAACCCGGAACTAGATGTCGGTATCGGGTTACGGTGCGATTACGGGAG 1080
  W  T  P  D  N  P  E  L  D  V  G  I  G  L  R  C  D  Y  G  R
```

FIG. 4B (cont.)

```
GTTTTTTGCATCAAAGAGTCTTTATGACCCATTGAAGAAAAGGAGGATCACTTGGGGTTA 1140
  F  F  A  S  K  S  L  Y  D  P  L  K  K  R  R  I  T  W  G  Y
TGTTGGAGAATCAGATAGTGCTGATCAGGACCTCTCTAGAGGATGGGCTACTGTTTATAA 1200
  V  G  E  S  D  S  A  D  Q  D  L  S  R  G  W  A  T  V  Y  N
TGTTGGAAGAACAATTGTACTAGATAGAAAGACCGGGACCCATTTACTTCATTGGCCCGT 1260
  V  G  R  T  I  V  L  D  R  K  T  G  T  H  L  L  H  W  P  V
TGAGGAAGTCGAGAGTTTGAGATACAACGGTCAGGAGTTTAAAGAGATCAAGCTAGAGCC 1320
  E  E  V  E  S  L  R  Y  N  G  Q  E  F  K  E  I  K  L  E  P
CGGTTCAATCATTCCACTCGACATAGGCACGGCTACACAGTTGGACATAGTTGCAACATT 1380
  G  S  I  I  P  L  D  I  G  T  A  T  Q  L  D  I  V  A  T  F
TGAGGTGGATCAAGCAGCGTTGAACGCGACAAGTGAAACCGATGATATTTATGGTTGCAC 1440
  E  V  D  Q  A  A  L  N  A  T  S  E  T  D  D  I  Y  G  C  T
CACTAGCTTAGGTGCAGCCCAAAGGGGAAGTTTGGGACCATTTGGTCTTGCGGTTCTAGC 1500
  T  S  L  G  A  A  Q  R  G  S  L  G  P  F  G  L  A  V  L  A
CGATGGAACCCTTTCTGAGTTAACTCCGGTTTATTTCTATATAGCTAAAAAGGCAGATGG 1560
  D  G  T  L  S  E  L  T  P  V  Y  F  Y  I  A  K  K  A  D  G
AGGTGTGTCGACACATTTTTGTACCGATAAGCTAAGGTCATCACTAGATTATGATGGGA 1620
  G  V  S  T  H  F  C  T  D  K  L  R  S  S  L  D  Y  D  G  E
GAGAGTGGTGTATGGGGGCACTGTTCCTGTGTTAGATGATGAAGAACTCACAATGAGGCT 1680
  R  V  V  Y  G  G  T  V  P  V  L  D  D  E  E  L  T  M  R  L
ATTGGTGGATCATTCGATAGTGGAGGGGTTTGCGCAAGGAGGAAGGACGGTTATAACATC 1740
  L  V  D  H  S  I  V  E  G  F  A  Q  G  G  R  T  V  I  T  S
AAGGGCGTATCCAACAAAAGCGATATACGAACAAGCGAAGCTGTTCTTGTTCAACAACGC 1800
  R  A  Y  P  T  K  A  I  Y  E  Q  A  K  L  F  L  F  N  N  A
CACAGGTACGAGTGTGAAAGCATCTCTCAAGATTTGGCAAATGGCTTCTGCACCAATTCA 1860
  T  G  T  S  V  K  A  S  L  K  I  W  Q  M  A  S  A  P  I  H
TCAATACCCTTTTAATTACCGGCTATCGCTATCCTTTTGTTATTGGTATTTATGTATC 1920
  Q  Y  P  F
TTAATTTTCTTTTAAACCTTTTTATTTGATAAATATTAGTTCTTGTTATTGTGCTTCTAG 1980
TAATAAATGAATGGTGTTATGGG                                      2003
```

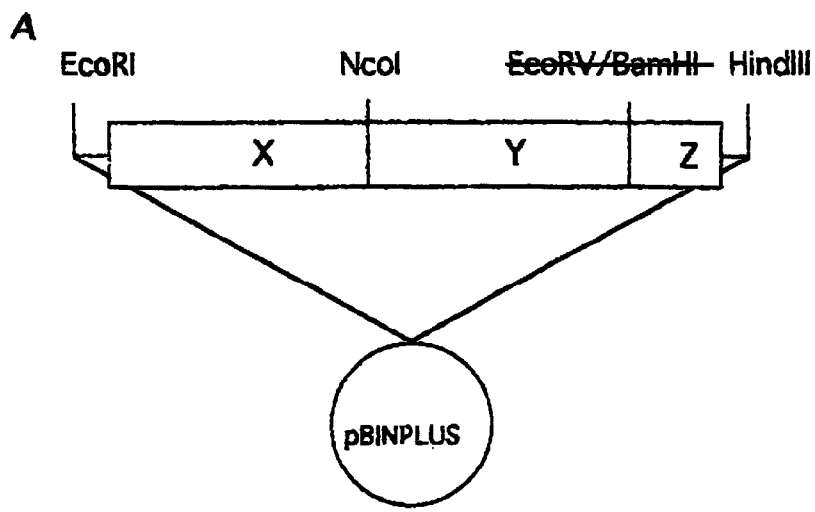
pVS1: enh.35S-AlMV-*sst-nos*
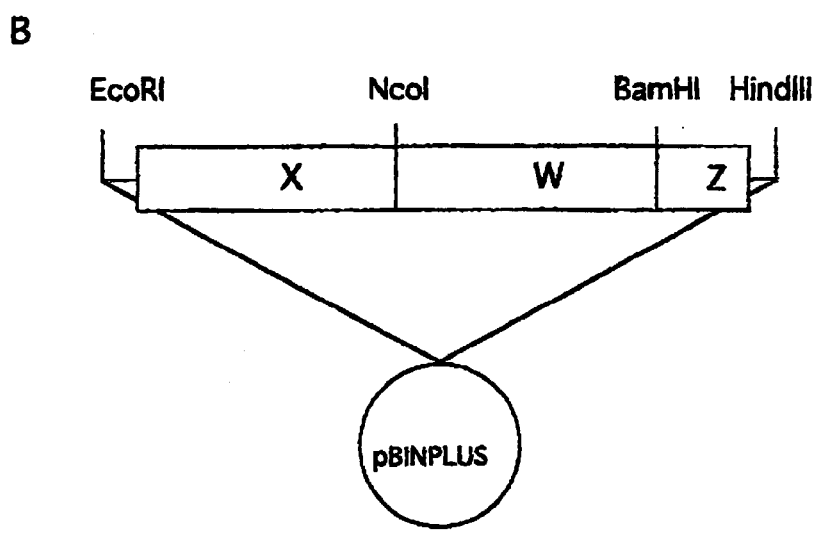
pVF1: enh.35S-AlMV-*fft-nos*
Fig. 5

DNA SEQUENCES ENCODING CARBOHYDRATE POLYMER SYNTHESIZING ENZYMES AND METHOD FOR PRODUCING TRANSGENIC PLANTS

This application is a 371 of PCT/NL96/00012 filed Jan. 8, 1996.

BACKGROUND OF THE INVENTION

This invention relates to nucleotide sequences encoding fructan synthesizing enzymes, a recombinant DNA sequence comprising one or more of said nucleotide sequences, a method for producing a genetically transformed host organism showing a modified fructan profile, and transformed plants or plant parts showing said modified fructan profile.

Fructans refer to a group of carbohydrate compounds in which one or more fructosyl-fructose linkages constitute a majority of the linkages. Fructans are fructosepolymers with usually, but not necessarily, one terminal glucosylunit [G-$(F)_n$, G=optional, $n \geq 2$]. The fructosyl-fructose linkages in fructans are of the β-2,6 or β-2,1 linkage type. Fructans with predominantly β-2,6 fructosyl-fructose linkages are usually called levan(s). Fructans with predominantly β-2,1 fructosyl-fructose linkages are usually called inulin(s).

Fructan biosynthesis is common in several bacterial, fungal and algal families and also in specific plant families, such as the Liliaceae (e.g. *Allium cepa*), Poaceae (e.g. *Lolium perenne*) and Asteraceae (e.g. *Helianthus tuberosus*). The function of fructans in bacteria and fungi is poorly understood. It has been suggested that fructans act as extracellular stores of carbohydrate that can be mobilized during periods of carbohydrate stress (Jacques, 1993). In plants, fructans can function as reserve carbohydrates which serve as a source of carbon for (re)growth (Meier and Reid, 1982). In fructan-storing crops, fructan synthesis is restricted not only to specific organs (e.g. the stems or tubers of *H. tuberosus*, the bulbs of Allium spp, the leaf bases and stems of grasses) but also specific cell types within these organs (usually the parenchyma cells). In these specific cell types, the vacuole is probably the location of both fructan biosynthesis and storage (Darwen and John, 1989; Wagner et al., 1983).

In bacteria, examples of fructan synthesizing bacteria are *Streptococcus mutans* and *Bacillus subtilus*, the biosynthesis of fructans from sucrose is catalysed by only one enzyme: levansucrase (EC 2.4.1.10) in *B. subtilus* (Dedonder 1966) and levansucrase, but also called fructosyltransferase, (FTF, EC 2.4.1.10) in *S. mutans* (Carlsson, 1970). Bacterial fructan synthesis proceeds via the direct transfer of fructose from a donor-sucrose (G-F) to sucrose or other acceptor molecules according to the following reversible reaction:

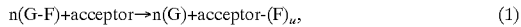

$$n(G-F)+\text{acceptor} \rightarrow n(G)+\text{acceptor-}(F)_n, \quad (1)$$

where n may be larger than 10.000

Water, hexoses, sucrose, oligosaccharides and levan may act as acceptor molecules for fructosyl units from sucrose (fructosyl donor).

Bacterial DNA sequences encoding FTF in *S. mutans* and levansucrase in *B. subtilus* are already described in the literature (Sato and Kuramitsu, 1986; Steinmetz et al. 1985). Bacterial genes from several sources were used to transform specific host plants which normally cannot synthesize fructans, thereby inducing fructan synthesis (see for example: Van der Meer et al., 1994; Ebskamp et al., 1994). A method to enhance the solid content of tomato fruits, using the levansucrase gene from *B. subtilus* and the dextransucrase gene from *Leuconostoc mesenretoides* is described in application WO 89/12386. A method to modify the fructan pattern in plants which normally cannot synthesize fructans, using the levansucrase-encoding ftf gene from *S. mutans* and the levansucrase-encoding SacB gene from *B. subtilus* is described in applications NL A 9300646 and WO 94/14970. The use of a levansucrase-encoding DNA sequence from *Erwinia amylovora*, which after integration in the host plant genome leads to the synthesis of levans, is described in DE 4227061 A1 and WO A 9404692. In all said applications, transgenic plants are described which are transformed with levansucrase genes from bacteria. Accordingly, these transgenic plants synthesize and accumulate fructans structurally comparable to those synthesized by the donor bacteria (Van der Meer et al., 1994; Ebskamp et al., 1994).

The present application differs from said applications in that it is related to fructosyltransferase-encoding DNA sequences derived from plants. These enzymes are structurally different from bacterial enzymes since there is no significant homology at the amino acid level and DNA level. Besides, the mechanism of fructan biosynthesis in plants is essentially different from that in bacteria. In contrast to fructan biosynthesis in bacteria, the formation of fructans in plants is mediated by more than one enzyme. For example, in *Relianthus tuberosus* (the Jerusalem Artichoke), fructan biosynthesis is catalysed by two enzymes: sucrose:sucrose fructosyltransferase (SST, EC 2.4.1.99) and fructan:fructan fructosyltransferase (FFT, EC 2.4.1.100). The SST and FFT from *H. tuberosus* are involved in the synthesis of β-2,1 linked fructans (inulin) and are therefore also designated as 1-SST and 1-FFT. 1-FFT has been purified from tubers of *H. tuberosus* (Lüscher et al., 1993, Koops and Jonker, 1994). The purification of SST has proven more difficult to achieve. A putative SST has been purified, at a very low yield, from several plant sources (Shiomi and Izawa, 1980; Praznik et al., 1990; Angenent et al., 1993). However, in none of these studies the purity of the enzyme has convincingly been shown. Furthermore, it has not conclusively been shown in these studies that the isolated enzyme does not represent an invertase.

Large quantities of 1-SST and 1-FFT have now been purified up to homogeneity from tubers of *H. tuberogus* (1-FFT: Koops and Jonker 1994) and their reaction mechanisms extensively investigated. 1-SST from *H. tuberosus* catalyses the initial step of fructan biosynthesis, the synthesis of the trisaccharide 1-kestose (1-[G-$(F)_2$]) from two molecules of sucrose (G-F), according to the following reaction:

$$G-F+G-F \rightarrow 1-[G-(F)_2]+G, \quad (2)$$

wherein G-F=sucrose, -F=fructosylunit, -G=glucosylunit, G=glucose

1-SST can also catalyse the formation of the tetrasaccharide 1,1-[G-$(F)_3$] and pentasaccharide 1,1,1-[G-$(F)_4$] (FIG. 3A). Therefore, 1-SST activity can be described by the following general reaction:

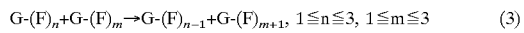

$$G-(F)_n+G-(F)_m \rightarrow G-(F)_{n-1}+G-(F)_{m+1}, \quad 1 \leq n \leq 3, \quad 1 \leq m \leq 3 \quad (3)$$

It has also been found that 1-SST from *H. tuberosus* to some extent can catalyse the transfer from a fructosyl unit from G-$(F)_n$, $1 \leq n \leq 3$, onto water.

The second enzyme, 1-FFT, catalyses the formation of fructans with a higher degree of polymerization. This enzyme catalyses a polymerization reaction by the transfer of fructosyl units between trisaccharides, tetrasaccharides and larger fructose polymers according to the following general reaction:

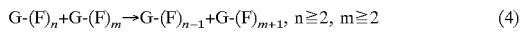

$$G\text{-}(F)_n + G\text{-}(F)_m \rightarrow G\text{-}(F)_{n-1} + G\text{-}(F)_{m+1}, \; n \geq 2, \; m \geq 2 \qquad (4)$$

It has also been found that 1-FFT catalyses the transfer of fructosyl units between sucrose (G-F) and galactose (Gal)-containing carbohydrates [(Gal)$_n$-G-F], also called galactans. For example, 1-FFT can catalyse the transfer of a fructosyl unit from G-(F)$_2$ onto raffinose (Gal-G-F) which results in the formation of [Gal-G-(F)$_2$]. It cannot be excluded that both 1-SST and 1-FFT from *H. tuberosus* can use other substrates as fructosyl acceptor.

Although 1-SST and 1-FFT have some overlapping activity—both enzymes can catalyse the formation of tetra and pentasaccharides (reactions 3 or 4)—1-SST and 1-FFT are distinctly different enzymes. The 1-SST and 1-FFT proteins have different physical properties and are encoded by different genes. 1-SST and 1-FFT have essentially different enzymic properties. 1-FFT is not able to catalyse the initial step of fructan synthesis (reaction 2), whereas 1-SST is not able to catalyse the formation of fructan polymers with a degree of polymerization higher then 5 [G-(F)$_n$, n>4]. In conclusion, with 1-SST activity alone, it is only possible to synthesize oligofructans from sucrose with a degree of polymerization of up to 5 [G-(F)$_n$, $2 \leq n \leq 4$]. To synthesize fructans with a higher degree of polymerization and using sucrose as a substrate, both 1-SST and 1-FFT are needed. With 1-FFT activity alone, it is not possible to synthesize fructans from sucrose. It was found by the present inventors that protein fractions containing purified 1-SST as well as purified 1-FFT could use sucrose as a sole substrate for the synthesis of fructans with a degree of polymerization of at least 15 [G-(F)$_{14}$, FIG. 3B].

Bacterial fructans differ from fructans in plants with respect to the degree of polymerization and branching type and, consequently, in chemical and physical properties. In general, fructans from plants are assembled from less than 1000 fructosylunits. Fructans from *H. tuberosus* are assembled from less than 100 fruccosylunits. Fructans synthesized by bacteria may comprise more than 10.000 fructosyl units. Plant and bacterial fructans therefore differ in their possible applications. For fructans with a relatively low degree of polymerization, such as those isolated from Asteraceae (e.g. Jerusalem Artichoke, chicory or dahlia), an application as phosphate substitute in calcium binding agents and detergents has already been worked out (WO91/17189). Other applications are related to the organoleptical properties of fructans. The sweetening strength of fructans G-(F)$_n$ decreases with an increasing degree of polymerization (increasing n-value). The sweetening strength of the oligofructans G-(F)$_2$ and G-(F)$_3$ approximates that of sucrose (G-F). The very long chain fructans such as those occurring in bacteria are not sweet at all. Very short chain fructans, such as those synthesized by sucrose:sucrose fructosyltransferase can therefore be used as sweeteners with the additional advantage that these sweet-tasting fructans are non-cariogenic and can withstand digestion in the digestive tract of humans, which opens possibilities for use as a low caloric sweetener. The short chain fructans, and also the longer chain fructans, can be used as the hydrophilic moiety of biosurfactants.

In contrast to the bacterial genes encoding levansucrase, which have already been cloned, the genes encoding SST and FFT have not been isolated before from plants. We found that the SST and FFT-encoding genes from plants, at the amino acid level, have no significant similarity to the known levansucrases and, at the DNA level, have no significant degree of homology to the levansucrase genes. For this reason it has not been possible to isolate the fructosyl transferase genes from plants using heterologous levansucrase probes from bacteria. It has also not been possible to isolate SST and FFT-encoding genes from plants using the amino acid sequences of the purified SST and FFT enzymes and their deduced oligonucleotide primers. The reason for this is that, although methods have been described for the purification of fructosyl transferases from plants, it has not been possible so far to obtain SST and FFT enzymes in sufficiently large amounts and with sufficiently high degrees of purity.

SUMMARY OF THE INVENTION

The object of this invention is to provide nucleotide sequences encoding SST and FFT.

Another object of this invention is to provide nucleotide sequences, obtained by recombination or mutagenesis of nucleotide sequences encoding SST or FFT, which encode enzymes having fructosyltransferase activity.

Yet another object of this invention is to provide a method for transforming non-fructan synthesizing crops into fructan-synthesizing crops by introduction of the SST and/or FFT-encoding genes.

Yet another object of this invention is to (partly) switch off the fructan synthesis in crops which normally synthesize fructans.

BRIEF DESCRIPTION OF THE DRAWINGS

FIGS. 4A–4B. Nucleotide sequence and deduced amino acid sequence of the isolated 1-SST (A) and 1-FFT (B) cDNA. The amino acids determined by amino acid sequencing (see also Table 1) of the purified 1-SST and 1-FFT proteins are underlined.

FIGS. 5A–5B. Gene constructs pVS1 (A) and pVF1 (B). The chimeric constructs consist of the enhanced CaMV35S promoter with ALMV translational enhancer (X), the coding sequence of sst (Y) or fft (W), and the nos termination signal (Z). Restriction sites which were used in the cloning procedure are indicated.

DETAILED DESCRIPTION OF THE INVENTION

Figure 1:
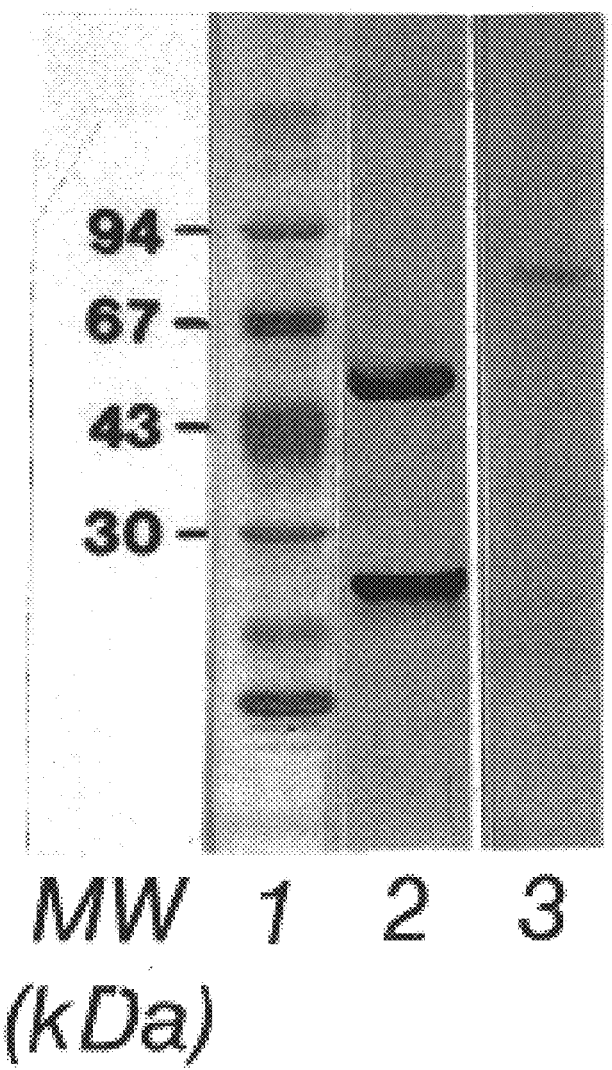
FIG. 1. Analysis of Mono Q fractions of 1-SST purification and Superdex HR 75 fractions of 1-FFT purification on SDS-PAGE. Lane 1, Molecular Weight marker (MW is given in kDa); lane 2, Mono Q fraction with 1-SST activity; lane 3, Superdex HR 75 fractions with 1—FFT activity.

Accordingly, this invention provides a DNA fragment having a nucleotide sequence SEQ ID. No. 1, as shown in FIG. 4A, or a homologous sequence having a degree of homology of at least 70% which encodes 1-sucrose:sucrose fructosyltransferase. Further, this invention provides a DNA fragment having a nucleotide sequence SEQ ID. No. 3 as shown in FIG. 4B or a homologous sequence having a degree of homology of at least 70% which encodes 1-fructan:fructan fructosyltransferase.

1-Sucrose:sucrose fructosyltransferase (1-SST) and 1-fructan:fructan fructosyltransferase (1-FFT) were purified from tubers of *Helianthus tuberosus*. Purified enzymes were cleaved into peptides by tryptic digestion, and the resulting peptide mixtures were separated by HPLC. N-terminal amino acid sequencing was performed for selected peptides. Amino acid sequences specific for 1-SST and 1-FFT were used to design degenerated oligonucleotide primers specific for 1-SST and 1-FFT, respectively, for use in RT-PCR. PCR was performed using cDNA as template, a tail-specific primer and the degenerated primers specific for either 1-SST or 1-FFT. First-strand cDNA was synthesized from poly(A)$^+$ RNA isolated from tubers from *H. tuberosus*. With the 1-SST-specific primer, RT-PCR resulted in a 450 bp specific fragment. With the 1-FFT-specific primer, RT-PCR resulted in a 800 bp specific fragment. The 450 and 800 bp PCR fragments were subsequently used to screen a cDNA library made from *H. tuberosus* tubers to isolate the full length cDNA sequences encoding 1-SST and 1-FFT, respectively.

The SST and FFT-encoding sequences from plants of the present invention induce, after insertion into the genome of a host organism, for example a plant, chances in the concentrations of carbohydrates containing at least one fructosyl unit (sucrose, oligofructans, fructans or galactans), or cause a change in the degree of polymerization of oligofructans, fructans or galactans. The present invention is related to said carbohydrates, since sucrose is the substrate for SST, oligofructans are products of SST, oligofructans and fructans with a higher degree of polymerization are substrates and products of FFT. Besides, said fructosyltransferase enzymes can also perform transfructosylation reactions with galactans of the raffinose series as fructosylacceptor.

The present invention includes DNA sequences which are at least 70% identical to the 1-SST-encoding sequence from *H. tuberosus*, irrespective of whether the homologous sequences are derived from other plant sources, or obtained by mutagenesis of fructosyltransferase-encoding sequences from plant sources or from microorganisms. It is preferred that the degree of homology is at least 80%, more preferred that the degree of homology is at least 85% and still more preferred that the degree of homology is at least 90%. It is most particularly preferred that the degree of homology is at least 95%.

The present invention includes DNA sequences which are at least 70% identical to the 1-FFT-encoding sequence from *H. tuberosus*, irrespective of whether the homologous sequences are derived from other plant sources, or obtained by mutagenesis of fructosyltransferase-encoding sequences from micro-organisms. It is preferred that the degree of homology is at least 80%, more preferred that the degree of homology is at least 85% and still more preferred that the degree of homology is at least 90%. It is most particularly preferred that the degree of homology is at least 95%.

The present invention includes also DNA sequences obtained by in vivo and in vitro recombination using SST and/or FFT-encoding sequences from plants and fructosyltransferase-encoding sequences from other prokaryotic or eukaryotic sources, including bacteria and fungi.

The present invention relates to SST-encoding DNA sequences from plants, which after insertion into the genome of a host organism induce the synthesis of oligofructans comprising of 2, 3 and/or 4 fructosyl units [G-(F)$_n$, $2 \leq n \leq 4$]. The present invention also relates to FFT-encoding DNA sequences from plants which after insertion into the genome of a host organism together with SST-encoding DNA sequences, induce the synthesis of fructans with a higher degree of polymerization [G-(F)$_n$, n>4].

The present invention also relates to chimeric gene constructs comprising sequences encoding SST or FFT, or part of the sequences, the sequences being present in the antisense orientation. Introduction of these antisense constructs in plants which can synthesize fructans, will cause inhibition of SST or FFT catalysed reactions or cause inhibition of SST or FFT expression.

The present invention relates to chimeric gene constructs encoding SST, or part of the sequence, the coding sequence being present in antisense orientation. Introduction of these antisense constructs into the genome of host plants which can synthesize fructans, such as species of the Asteraceae, Liliaceae and Poaceae family, reduce or block the conversion of sucrose into oligofructans [G-(F)$_n$, $2 \leq n \leq 4$]. Since only SST is able to catalyse the first step of fructan synthesis (reaction 2), in such transgenic plants, also the synthesis of fructans with a higher degree of polymerization, [G-(F)$_n$, n>4], will be reduced or blocked and these plants will accumulate sucrose rather than fructans.

The present invention relates to chimeric gene constructs encoding FFT, or part of the sequence, the coding sequence being present in the antisense orientation. Introduction of these antisense constructs into the genome of host plants which can synthesize fructans, reduce or block the conversion of oligofructans [G-(F)$_n$, $2 \leq n \leq 4$] into fructans with a higher degree of polymerization [G-(F)$_n$, n>4]. Transgenic plants thus obtained will accumulate oligofructans, rather than fructans with a higher degree of polymerization.

Accordingly, the present invention provides a method for producing a genetically transformed host organism showing a modified fructan profile, which comprises the steps of:

i) preparing a chimeric gene construct comprising one or more DNA fragments as defined above, or said DNA fragments in the inverted orientation, operably linked to a promoter sequence active in said host organism and a terminator sequence active in said host organism, ii) introducing the chimeric gene construct into the genome of the host organism.

The host organism may be a microorganism or a plant. In case the host organism is a plant, the method additionally comprises the step of iii) regenerating the transformed plant cells to transgenic plants.

More specifically the method of the invention comprises the following steps:

a. construction of a chimeric gene comprising essentially the following sequences:
   a promoter which ensures the formation of a functional RNA or protein in the intended target organism, target organs, tissues or cells,
   a DNA sequence encoding SST or FFT,
   a transcription terminator operationally connected to the DNA sequence, the SST or FFT-encoding DNA sequence being functionally connected to a promoter,
   a DNA sequence encoding a targeting signal or a transit peptide which ensures targeting of SST or FFT to a specific subcellular compartment;

b. introduction of the chimeric gene into the genome of a host organism so as to obtain genetic material comprising the DNA sequence and c. regeneration of the genetic material in a transformed host organism.

In the recombinant DNA of the present invention, the DNA sequence encoding SST or FFT is preferably linked to a regulatory sequence that ensures proper expression of the DNA sequence in a host organism, such as a bacterium, a yeast, an alga or a plant, at a sufficiently high expression level. Regulatory sequences are a promoter, a termination signal and a transcription or translational enhancer. A promoter can be the 35S promoter of the cauliflower mosaic virus (CaMV), or a sugar-inducible promoter like the patatine promoter or an organ-specific promoter like the tuber-specific potato proteinase inhibitor II promoter or any other inducible or tissue-specific promoter.

In the recombinant DNA of the present invention, the SST or FFT-encoding DNA sequence is preferably linked to regulatory sequences that are operative in plants and that ensure proper expression of the DNA sequence in the different plant organs, tissues or cells. A highly preferable promoter is a promoter which is active in organs and cell types which normally accumulate sucrose (the primary substrate for fructan synthesis). The production of fructans is particularly advantageous in organs storing large amounts of sucrose, such as the tap roots of sugar beet or the stems of sugar cane. Besides roots, other organs or cell types are involved in the synthesis, processing, transport and accumulation of sucrose. Therefore, SST or FFT-encoding sequences are also suitably expressed in leaves, stems, roots, tubers, reproductive organs, and seeds.

In the recombinant DNA of the present invention, the DNA sequence encoding SST or FFT contains, or is linked to, a sequence encoding a transit peptide which directs the SST or FFT mature protein to a subcellular compartment containing sucrose. The production of fructans is particularly advantageous in the vacuole which can accumulate very high concentrations of sucrose (up to 900 mol m$^{-3}$). Besides the vacuole, other subcellular compartments are involved in the synthesis (cytoplasm), processing (cytoplasm, mitochondria, plastids) and transport (cell wall, cytoplasm) of sucrose. The present invention therefore relates to the use or sequences that allow targeting of the SST or FFT product to specific subcellular compartments, such as the vacuole, the cell wall, mitochondria, plastids and cytoplasm.

The present invention also relates to gene constructs, comprising a sequence encoding SST or FFT, or part of the sequences, the coding sequence being present in the anti-sense orientation. In these gene constructs, the SST or the FFT-encoding sequence is preferably linked to a promoter that ensures the formation of an antisense RNA in the cell types which normally were able to synthesize fructans.

The recombinant DNAs of the present invention may also encode proteins having herbicide resistance, plant growth promoting, plant growth inhibiting, anti-fungal, anti-bacterial, anti-viral and/or anti-nematode properties or conferring stress resistance. The recombinant DNAs of the present invention may further encode proteins which induce sterility. In case that the DNA is to be introduced into a heterologous organism it may be modified to remove known mRNA instability motifs (such as AT rich regions); and polyadenylation signals, and/or codons which are preferred by the organism, into which the recombinant DNA is to be inserted, are used so that expression of the thus modified DNA in the host organism is higher than that obtained by expression of the unmodified recombinant DNA in the same host organism.

The present invention also provides the transformed host organism, especially a transformed plant, produced by the above method. The invention preferably includes agricultural, forage, vegetable, ornamental and fruit crops, more preferably sugar beet, sugar cane, potato, petunia, alfalfa, soybean, rice, ryegrass, thimothygrass, wheat, barley, sorghum, maize, chicory, Jerusalem artichoke, tulip, melon, onion, garlic, tomato, strawberry, apple and pear. Moreover, the invention includes a plant cell, seed, fruit, seedling or any plant part harbouring recombinant DNA, comprising a sequence encoding SST or FFT as defined herein. Further, this invention includes the progeny of the transformed plants which contain the DNA stably incorporated and heritable in a Mendelian manner and/or the seeds of such plants and such progeny.

EXPERIMENTAL

Purification of 1-SST

Tubers of *Helianthus tuberosus* 'Colombia' were used for the extraction of 1-SST and 1-FFT. Tubers were harvested in August–September, during the period of rapid tuber growth and massive fructan accumulation. Tubers were washed and frozen in liquid nitrogen. Four hundred gram of frozen tubers (–80° C.) were pulverized and immediately thereafter homogenized in a Waring blender in 900 cm$^3$ 50 mol m$^{-3}$ phosphate (P) buffer, pH 6.5, containing 10% (w/v) glycerol, 1 mol m$^{-3}$ MgSO$_4$, 1 mol m$^{-3}$ Na$_2$EDTA, 1 mol m$^{-3}$ PMSF (Sigma, USA) 1 mol m$^{-3}$ DTT, 1.5% (w/v) PVPP and 20 mmol m$^{-3}$ Na$_2$S$_2$O$_5$. The homogenate was filtered through three layers of Miracloth and centrifuged at 17,000 g for 1 h.

The protein extract was kept at 4° C. and adjusted to 45% saturation with (NH$_4$)$_2$SO$_4$. The insoluble proteins were pelleted by centrifugation (10,000 g, 30 min) and discarded.

The 45% supernatant was brought to 70% saturation by further addition of $(NH_4)_2SO_1$. The pellet, obtained after a second centrifugation step, was redissolved in 60 cm$^3$ 50 mol m$^{-3}$ phosphate (P) buffer, pH 6.5, 1 mol m$^{-3}$ DTT and 1 mol m$^{-3}$ PMSF (Sigma, USA), and desalted by dialysis against 10 mol m$^{-3}$ P-buffer, pH 6.5, 1 mol m$^{-3}$ PMSF and 1 mol m$^{-3}$ DTT, for 16 h. After buffer replacement, dialysis was continued for another 3 h. The whole procedure was performed at temperatures between 0 and 4° C. The centrifuged dialysate (30,000 g, 30 min) was applied onto a 25×120 mm Q Sepharose Phast Flow column (4° C.), which had been prewashed with 10 mol m-3 bis Tris, pH 6.5, 1 mol m$^{-3}$ DTT, 1 mol m$^{-3}$ PMSF and 5 mol m$^{-3}$ EDTA in Milli Q water. Bound proteins were eluted with an NaCl gradient (0–300 mol m$^{-3}$) in the same buffer at a flow rate of 5 cm$^3$ min$^{-1}$. 1-SST eluted at 200–250 mol m$^{-3}$ NaCl.

The Q Sepharose fractions were adjusted to 400 mol m$^{-3}$ with solid $(NH_4)_2SO_4$. Fractions of 20 cm$^3$ were loaded onto a 15×50 mm column of Phenyl Sepharose High Performance or Phenyl Sepharose High Substitution, which where pre-equilibrated with 10 mol m$^{-3}$ bis Tris buffer, pH 6.5, containing 500 mol m$^{-3}$ $(NH_4)_2SO_4$, 1 mol m$^{-3}$ DTT, 1 mol m$^{-3}$ PMSF, 2 mol m$^{-3}$ EDTA and 0.1% CHAPS (buffer A) at 12° C. Elution of bound proteins was carried out using a linear gradient of buffer A (100–0%) without $(NH_4)_2SO_4$, containing 25% (v/v) ethylglycol, at a flow rate of 1 cm$^3$ min$^-$. 1-SST eluted at 100 mol m$^{-3}$ $(NH_4)_2SO_4$.

Phenyl Sepharose fractions up to 10 cm$^3$ were injected onto a 5×50 mm Concanavalin A Sepharose column, pre-washed in 20 mol m$^{-3}$ bis-Tris, pH 6.5, 250 mol m$^{-3}$ NaCl, 0.5 mol m$^{-3}$ $CaCl_2$, 0.5 mol m$^{-3}$ $MnCl_2$, 1 mol m$^{-3}$ DTT and 1 mol m$^{-3}$ PMSF. Bound 1-SST was eluted with 500 mol m$^{-3}$ α-$CH_3$-mannopyranoside in the same buffer.

Active fractions of one Concanavalin A-run were pooled and applied to a 5×200 column packed with spherical (15 μm) hydroxylapalite (Merck, Germany). The column was pre-equilibrated in 2 mol m$^{-3}$ $CaCl_2$, 10 mol m$^{-3}$ NaCl, 1, mol m$^{-3}$ DTT, 1 mol m$^{-3}$ PMSF and 0.1% CHAPS (buffer A). Proteins bound to the column were eluted with stepped gradient of buffer A and 500 mol m$^{-3}$ potassium phosphate buffer, pH 6.5, at a flow rate of 0.5 ml min$^{-1}$. 1-SST eluted at 75–100 mol m$^{-3}$ potassium phosphate.

Active fractions of one hydroxylapatite run were pooled and applied onto a 5×50 mm Mono Q-column which was pre-equilibrated with 10 mol m$^{-3}$ P-buffer, pH 6.5, 1 mol m$^{-3}$ DTT, 1 mol mu$^{-3}$ EDTA and 0.1% CHAPS. Bound proteins were eluted with an NaCl gradient (0–500 mol m$^{-3}$) at a flow rate of 0.5 cm$^3$ min$^{-1}$. 1-SST eluted at 250 mol m$^{-3}$ NaCl.

All columns, column packings and chromatography equipment were obtained from Pharmacia (Sweden), unless indicated otherwise.

Purification of 1-FFT

A crude protein extract was obtained from tubers of *H. tuberosus* as described for the purification of 1-SST. The supernatant of the crude protein extract, as obtained after centrifugation was adjusted to 45% saturation with $(NH_4)_2SO_4$ and stirred for 1 h. The insoluble proteins were pelleted by centrifugation at 10,000 g for 30 min. The pellet was redissolved in 60 cm$^3$ 50 mol m$^{-3}$ P-buffer, pH 6 5, 1 mol m$^{-3}$ DTT and 1 mol m$^{-3}$ PMSF, and dialyzed overnight against 10 mol m$^{-3}$ citrate/phosphate (C/P) buffer, pH 4.5, containing 1 mol m$^{-3}$ PMSF and 1 mol m$^{-3}$ DTT. The contents of the dialysis tubing was readjusted to pH 6.5 with 0.2 M $Na_2HPO_4$ and the insoluble proteins were removed by centrifugation at 30.000 g for 1 h. The supernatant was loaded onto a 25×120 mm column of Q Sepharose Phast Flow (Pharmacia) pre-equilibrated with 10 mol m$^{-3}$ P-buffer, pH 6.5, 1 mol m$^{-3}$ DTT and 1 mol m$^{-3}$ PMSF in Milli Q water ((Millipore B.V., The Netherlands). The column was cooled to 4° C. Bound proteins were eluted with a positive NaCl gradient at a flow rate of 5 cm$^3$ min$^{-1}$. 1-FFT eluted at 200–250 mol m$^{-3}$ NaCl.

Solid $(NH_4)_2SO_4$ was added to the Q Sepharose fractions to give a final concentration of 750 mol m$^{-3}$ with. Fractions of 5 cm$^3$ were loaded onto a 15×50 mm column of Phenyl Sepharose High Performance (Pharmacia), pre-equilibrated with 10 mol m$^{-3}$ P-buffer, pH 6.5, containing 750 mol m$^{-3}$ $(NH_4)_2SO_4$ and 1 mol m$^{-3}$ DTT. Bound proteins were eluted with a negative $(NH_4)_2SO_4$ gradient at a flow rate of 1 cm$^3$ min$^{-1}$ at 12° C. 1-FFT eluted at 450–400 mol m$^{-3}$ $(NH_4)_2SO_4$.

Phenyl Sepharose fractions (up to 4 cm$^3$) were injected onto a Hiload 16×600 mm Superdex 75 prep grade column (Pharmacia) pre-washed in 10 mol m$^{-3}$ P-buffer, pH 6.5, and 1 mol m$^{-3}$ DTT. Proteins were eluted in the same buffer at a flow rate of 0.5 cm$^3$ min$^{-1}$ at 20° C. 1-FFT eluted 95–105 min after injection.

1-FFT and 1-SST assays

The 1-FFT activity of column fractions was routinely assayed at 35° C. Aliquots of 25 mm$^3$ were mixed with 25 mm$^3$ 0.3 g Neosugar P (Meiji Seika Kaisha, Ltd, Tokyo, Japan: Neosugar consists of 1% hexoses, 4% sucrose, 42% G-$(F)_2$, 44% G-$(F)_3$ and 7% G-$(F)_4$) per cm$^3$ of 100 mol m$^{-3}$ C/P-buffer, pH 6.5. After 3 h, the reaction was stopped by boiling the incubation mixture in a waterbath for 5 min. A net gain of $GF_4$ was taken as a measure for 1-FFT activity.

For 1-SST activity, 15 mm$^3$ column fractions were mixed with 15 mm$^3$ 500 mol m$^{-3}$ GP in 100 mol m$^{-3}$ C/P-buffer, pH 5.0 and incubated for 3 h at 35° C. $GF_2$ synthesis was taken as a measure for 1-SST activity.

Analysis of sugars and fructans

Sucrose and oligofructans were analyzed by RP-HPLC using a 2.1×220 mm Speri-5 RP 18 column (Brownlee Labs, Santa Clara, USA). Milli Q water was used as the eluant at a flow rate of 0.3 cm$^3$ min$^{-1}$ at 37° C. Glucose and fructose were quantified on a 6.5×300 mm Shodex SC-1011 column (Millipore B.V., Waters Chromatography Division, The Netherlands) run at 85° C. with Milli Q water at 0.75 cm$^3$ min$^{-1}$. Sugars were detected with a 2142 refraction index detector (RID, Pharmacia). Identification of oligofructans was by comparison of their retention times with those from the oligofructans purified from Neosugar P or from *H. tuberosus* and by the glucose/fructose ratios of the individual oligofructans (Koops and Jonker, 1994).

HPAEC analyses of oligofructans and fructans with a higher degree of polymerization were performed on a Dionex Series 4000 ion chromatograph equipped with 250×4 mm CarboPac PA1 anion exchange column and a 25×3 mm CarboPac PA guard column. Fructans were separated with a 60 min linear gradient of 0.25 to 0.4 mol m$^{-3}$ NaAc in 0.1 mol m$^{-3}$ NaOH at a flow rate of 1 ml min$^{-1}$. Detection was by pulsed amperometry (PAD) with a gold-working electrode. The applied potential of a pulse was kept at 0.1, 0.6 and −0.6 V for 0.5, 0.1 and 0.05 seconds, respectively. Rhamnose was used as an internal standard. Fructans were identified by comparison of their retention times with those of fructan standards isolated and purified from *H. tuberosus* according to the method of Heinze and Praznik (1991).

Amino acid sequencing of 1-SST and 1-FFT

Mono Q fractions of 1-SST or Superdex 75 fractions of 1-FFT were desalted and concentrated by centrifugation in Centricon- 10 (2 cm$^3$) ultrafiltration devices (Grace B.V., Amicon division, The Netherlands) and subsequently collected by precipitation in 80% (v/v) aqueous acetone at $-20°$ C. 1-SST and 1-FFT (each 50 μg) were dissolved in SDS-buffer (Laemmli, 1970) and separated on a pre-cast Excel-Gel SDS, gradient 8–18. Proteins were stained with Coomassie Brilliant Blue according to Rosenfeld et al. (1992). The stained 1-SST (2 bands; due to its intrinsic lability 1-SST is cleaved by the SDS treatment) and 1-FFT bands were excised with a scalpel and washed, dried and partially rehydrated according to the procedure of Rosenfeld et al. (1992). Sequencing-grade trypsin (0.5 μg; Boehringer, Germany) was added to the gel slice, and in-gel digestion of the proteins was carried out for 4 h at 30° C. The resulting peptides were recovered by two extractions of 20 min each, with 50 μl acetonitrile, water, trifluoracetic acid and Tween 20 (60:40:0.001:0.0002, v/v). The resulting peptide mixture was separated by preparative RP-HPLC on a 9.3×250 mm SuperPac Pep-S column (Pharmacia) eluted with a linear gradient of 0.1% TFA in 0 to 60% aqueous acetonitrile at a flow rate of 4 ml min$^{-1}$. Individual peptide fractions were collected manually and stored at $-80°$ C. The amino acid sequences of selected peptides were determined by Edman degradation, using a model 417A pulse-liquid sequenator, connected on-line to a model 120A RP-HPLC unit (Applied Biosystems). Amino acid sequences specific for 1-SST or FTT were translated into the corresponding degenerated DNA sequences (Example 1, Table 1), which, in turn, were used as primers for ACR.

DNA methodology

DNA and RNA isolation, subcloning, restriction analysis and sequencing were performed using standard methods described in molecular biology manuals (Sambrook et al. 1989, Ausubel et al. 1994).

cDNA synthesis

Poly (A)$^+$RNA was isolated from tubers of *H. tuberosus* 'Colombia'. Single stranded cDNA was synthesized by reverse transcriptase from 10 μg poly(A)$^+$RNA by priming the poly(A)$^+$RNA with the following tail specific primer: 5'-CCGAATTCAATACGACTCACTATAGCG(T)$_{15}$-3'

PCR

Degenerated oligonucleotides specific for 1-SST or 1-FFT and the tail specific primer, 5'-CCGAATTCAATACGACTCACTATAGCG-3' were used for amplification of the single strand cDNA. PCR was performed in 50 μl PCR buffer (Life Technologies), containing 100 pmol cDNA template, 100 pmol of the tail specific primer and 100 pmol of primers specific for 1-SST or 1-FFT. Amplification involved 30 cycles of denaturing (1 min, 92° C.), annealing (1 min, 42° C.) and amplification (1 min, 72° C.). The resulting fragments were electrophoresed in 0.7% agarose, excised from the gel, isolated from the agarose matrix and subcloned into pMOSBlue vector (Amersham). 1-SST and 1-FFT specific fragments generated by PCR were used to screen a Uni-ZAP XR cDNA library.

Construction and screening of a cDNA library

Ten μg of poly(A)$^+$RNA isolated from tubers of *H. tuberosus* 'Colombia' was used as starting material for the construction of an Uni-ZAP XR cDNA library (Stratagene). Construction, plating and screening of the library were performed according to the protocols developed by Stratagene (La Jolla, Calif., cat. no. 237211). $^{32}$P-labelled DNA probes specific for 1-SST or 1-FFT were prepared by random oligonucleotide priming and used to screen about 100.000 plaques. Hybridization and washing of Hybond-N membrane were performed under high stringency conditions (hybridization at 65° C., final wash step with 0.1×SSC, 0.1% SDS, 65° C.). Positive clones were purified, the pbluescript phagemids excised from the Uni-ZAP vector using the Exassist/Solr system (Stratagene) and the inserts by restriction enzyme analysis, hybridization and sequencing.

Analysis of transgenic plants

Analysis of sugars and fructans 50 mg of leaf tissue was frozen in liquid $N_2$ and homogenized in 0.1 cm$^3$ Milli Q water in an Eppendorf tube. The homogenate was heated to 90° C. for 5 min, then centrifuged at 14,000 g for 10 min. The clear supernatant was analysed by TLC: 2 μl of the supernatant was spotted onto a silica gel G 1500 (Schleicher & Schuell) plate. TLC plates were developed two times with either acetone, water (9:1, v/v), or butan-1-ol, propan-2-ol and water (3:12:4, v/v). Carbohydrates were visualized by spraying the TLC plates with urea-phosphoric acid (Wise et al. 1955).

1-FFT assay

Leaf tissue (50 mg) was frozen in liquid $N_3$ and homogenized in an Eppendorf tube in 0.1 cm$^3$ 25 mol m$^{-3}$ phosphate (P) buffer, pH 6.5, containing, 2 mol m$^{-3}$ MgSO$_4$, 2 mol m$^{-3}$ Na$_3$EDTA, 2 mol m$^{-3}$ PMSF (Sigma, USA) 2 mol m$^{-3}$ DTT, 1.5% (w/v) soluble PVPP (Merck) and 20 mol m$^{-3}$ Na$_2$S$_2$O$_5$. The homogenate was centrifuged at 14,000 g for 10 min at 4° C. The clear supernatant was used for the 1-FFT assay. Fifty μl of the supernatant was mixed with 50 μl of an assay mixture, containing 2 mol m.$^{-3}$ G-(F)$_3$, 80 mol m$^{-3}$ G-(F)$_4$, 50 mol m$^{-3}$ citrate/phosphate buffer, pH 5.5, and 0.02% (w/v) NaN$_3$. The assay mixture was incubated in the dark at 28° C. Samples of 15 μl were taken after 4, 20, 44 and 68 h of incubation, and analysed by TLC.

EXAMPLES

Example 1

Figure 3:
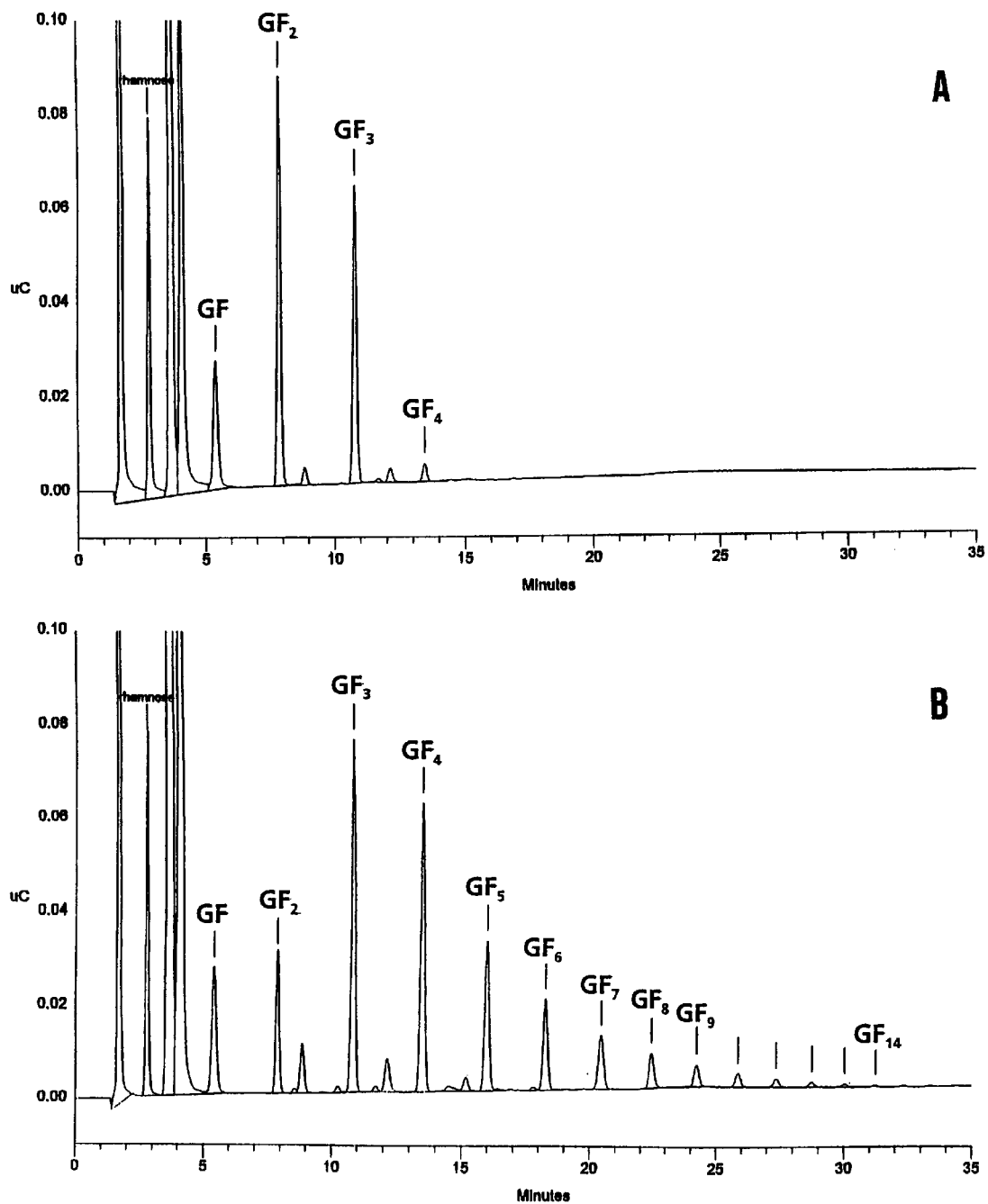
FIGS. 3A–3B. HPAEC separations of oligofructans synthesized from sucrose by purified 1-SST (A) and by a mixture of purified 1-SST and purified 1-FFT (B). The reactions were performed in 100 mol m$^{-3}$ sucrose, 2 mol m$^{-3}$ DTT, 10 mol m$^{-3}$ citrate/phosphate buffer, pH 5.0, 0.01% Na-azide at 25° C. Reaction time was 80 h. Reaction was stopped by boiling the reaction mixture for 5 min. Rhamnose was used as an internal standard.

Purification of the sucrose:sucrose fructosyltransferase (1-SST) and fructan fructosyltransferase (1-FFT), and isolation of 1-SST and 1-FFT- encoding cDNAs 1-SST and 1-FFT were purified from tubers of *Helianthus tuberosus* using precipitation techniques, several successive chromatography procedures and electrophoresis. Fractions with 1-SST-activity, eluting from the Mono Q column gave one band after native PAGE. 1-SST is cleaved by SDS, therefore analysis by SDS PAGE yielded two bands of 27 and 55 kDa (FIG. 1, lane 2). Fractions with 1-FFT-activity eluting from the Superdex 75 gel permeation column gave on SDS PAGE one band with an estimated molecular weight of 70 kDa (FIG. 1, lane 3). 1-SST alone was able to synthesize oligofructans from sucrose as a sole substrate (FIG. 3A, 80 h of incubation). By recombining purified 1-SST with purified 1-FFT, sucrose could be converted into fructans with a deree of polymerization of at least 15 [G-(F)$_{14}$, FIG. 3B, 80 h of incubation].

Figure 2:
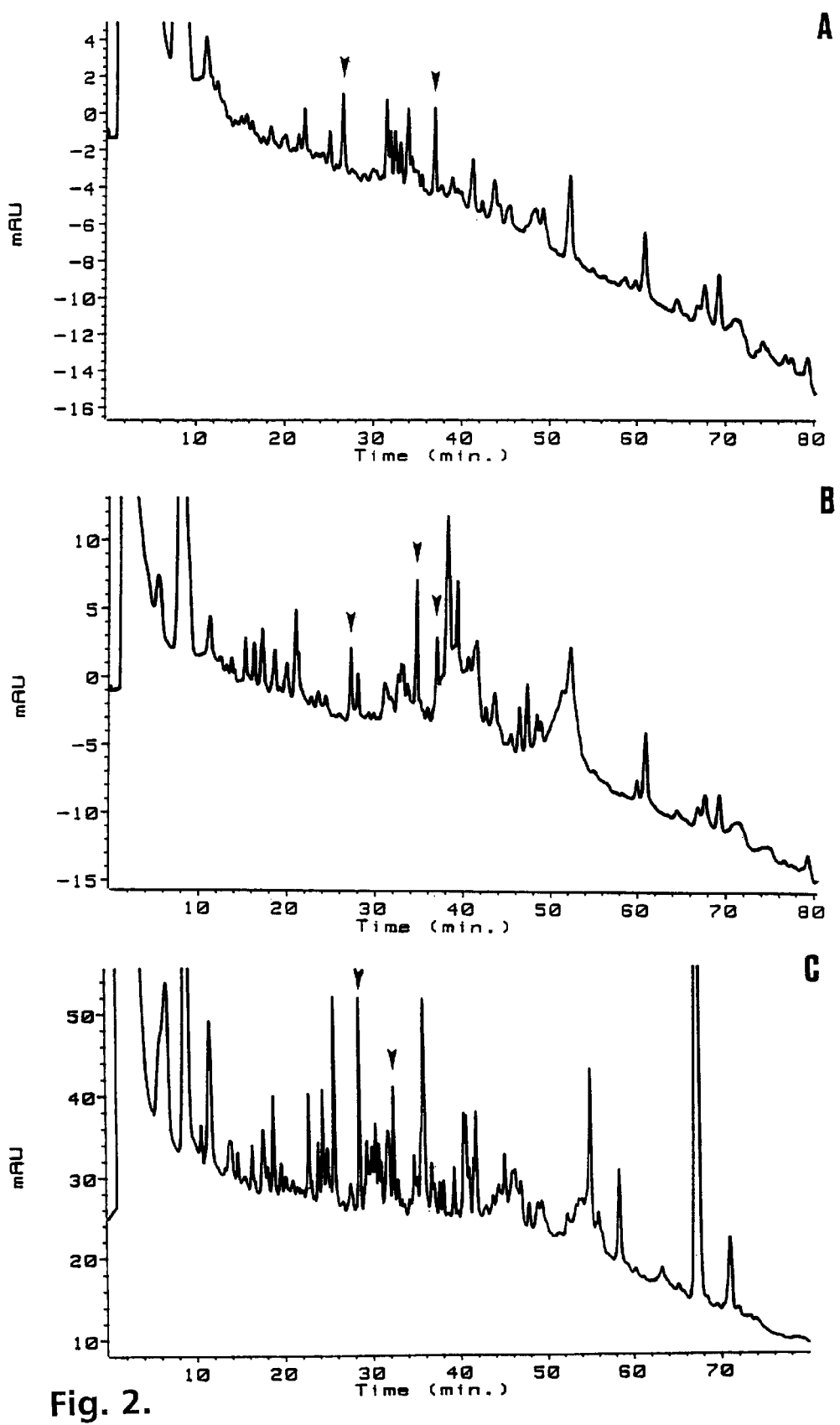
FIGS. 2A–2C. RP-HPLC separations of tryptic digests of: a. the 25 kDa polypeptide of 1-SST (A); b. the 55 kDa polypeptide of 1-SST (B); c. the 70 kDa 1-FFT polypeptide (C). Free eluting peptide fractions indicated with arrows were collected manually and subjected to amino acid sequencing.

For amino acid sequencing by the Edman (phenylisothiocyanate) degradation method, the 27 kDa (1-SST), 55 kDa (1-SST) and 70 kDa (1-FFT) protein bands were excised from the SDS PAGE gel and subjected to proteolytic digestion by trypsin. The resulting peptide mixtures were separated by RP-HPLC in separate runs (FIGS. 2A–C). The peptides eluting after 26 min and 37 min (both from the 25 kDa fragment of 1-SST, FIG. 2A), 27 min, 34 min and 37 min (from the 55 kDa fragment of 1-SST, FIG. 2B), 28 min, and 32 min (from 1-FFT, FIG. 2C, the fraction eluting at 32 min contained the peptides 7 and 8) were collected manually and subjected to N-terminal amino acid sequencing (Table 1).

TABLE 1

Amino acid sequences of selected peptides obtained after
tryptic digestion of 1-SST (25 and 55 kDa polypeptides)
and 1-FFT, and separation of the resulting peptide mixtures
by RP-HPLC

| protein | amino acid sequence | DNA sequence of PCR-primer |
|---|---|---|
| 1 1-SST,25 kDa | ADVLF??TTSEGSVAR | |
| 2 idem | EQLPVYFYIAK | 5'-GARCARYTNCCNGTNTAYTTYTAYATH GCNAAR-3' |
| 3 1-SST,55 kDa | VVLDLETK | |
| 4 idem | FRDPSTLWL?PDGEY | |
| 5 idem | GWANIL | |
| 6 1-FFT | GWATVYNVGR | 5'-GGNTGGGCNACNGTNTAYAAY-3' |
| 7 idem | LLVDHSIVEGFAQGGR | 5'-ATHGTNGARGGNTTYGCNCAR-3' |
| 8 idem | VGESDS | |

Amino acid sequences 2 (1-SST, 25 kDa), 6 and 7 (1-FFT) were used to design DNA primers specific for 1-SST or 1-FFT which were used for PCR. PCR using primers 2, 6 or 7 yielded DNA of about 450, 600 bp and 300 bp, respectively. Nested PCR, using oligonucleotide 7 as specific primer and the 800 bp PCR fragment as template, again yielded the 300 bp PCR fragment which indicated that the 300 bp fragment is included in the 800 bp fragment.

An Uni-ZAP cDNA library constructed from mRNA isolated from *H. tuberosus* tubers was screened with either the 450 bp 1-SST or the 800 bp 1-FFT fragment. Screening of about 100.000 cDNA clones yielded about 20 positive clones hybridizing to the 450 bp fragment and 25 clones hybridizing to the 800 bp fragment. DNA of clones hybridizing to the 450 bp fragment did not hybridize to the 800 bp fragment and vice versa. Positive clones were purified, the pBluescript phagemids excised from the uni-ZAP vector and the insert characterized by restriction enzyme analysis, hybridization and sequencing.

The DNA sequences of 1-SST and 1-FFT and their corresponding amino acid sequences are presented in FIG. 4A and FIG. 4B, respectively. Sequence ID. No. 1, encoding 1-SST, has an open reading frame of 1890 base pairs and encodes a protein of 630 amino acid residues. On DNA level, 1-SST shows a 68% identity with soluble acid β-fructofuranosidase (=acid invertase) cDNA from carrot (*Daucus carota*). At the amino acid level, 1-SST shows a 66% similarity with soluble acid β-fructofuranosidase from carrot.

Sequence ID. No. 3, encoding 1-FFT, has an open reading frame of 1845 base pairs and encodes a protein of 615 amino acid residues and a molecular weight of about 69 kDa. This corresponds to the molecular weight of the purified 1-FFT protein as established by SDS-ACAGE (Koops and Jonker, 1994). On DNA level, 1-FFT shows a 65% identity with soluble acid β-fructofuranosidase (=acid invertase) cDNA from carrot. At the amino acid level, 1-FFT shows a 60% similarity with soluble acid β-fructofuranosidase from carrot.

Although 1-SST and 1-FFT have a relatively high degree of homology with acid invertase it has been shown that 1-SST or 1-FFT and invertase are distinctly different enzymes. It has been shown that 1-SST and 1-FFT are unable to catalyse the hydrolysis of sucrose (invertase activity). Hydrolytic activity of purified 1-SST and 1-FFT against sucrose has been tested at a range of pH's and sucrose concentrations. There was no significant invertase activity under any of these conditions (Koops and Jonker 1994). No homology higher than 68% was observed between the DNA sequence encoding 1-SST and any known DNA sequence within the PDB, GENBANK, GENBANK updates, EMBL and EMBL updates nucleotide sequence databases. No homology higher than 65% was observed for the DNA sequence encoding 1-FFT with any known DNA sequence within the PDB, GENBANK, GENBANK updates, EMBL and EMBL updates nucleotide sequence databases.

Example 2

Construction of a chimeric sst gene

The full length sst cDNA clone, designated pSST 103, was used for the introduction of an NcoI site at the ATG (position 34), and a EcoRV site downstream of the stopcodon (at position 1924) using PCR. From the plasmid pMOG18 (Pen et al., 1992) which contains the enhanced CaMV35S promoter, ALMV leader sequence, uidA gene and the nos terminator sequence, the uidA coding sequence was replaced by the sst cDNA. pMOGl8 was digested with BamHI, filled in with Klenow DNA polymerase, and digested with NcoI. The sst PCR fragment, cut with NcoI and EcoRI, was ligated into this vector, resulting in the clone pSST217. The EcoRI/HindII fragment of pSST217 containing the complete chimeric construct (enh.35S+ALMV-sst-nos) was cloned into the EcoRI and HindIII site of pBIN-PLUS (Van Engelen et al., 1995), a binary plant transformation vector derived from pBINl9 (Bevan, 1984) resulting in plasmid pVSl (FIG. 5A).

Example 3

Construction of a chimeric fft gene

The full length fft cDNA clone, designated pFFT 111, was used for the introduction of an NcoI site at the ATG (position 29), and a BamHI site downstream of the stopcodon (at position 1874) using PCR. From the plasmid pMOG18 (Pen et al., 1992) which contains the enhanced CaMV35S promoter, ALMV leader sequence, uidA gene and the nos terminator sequence, the uidA coding sequence was replaced by the fft cDNA. The PCR fragment digested with NcoI and BamHI was ligated into the pMOG18 vector digested with NcoI and BamHI, resulting in clone pFFT209. The HindIII/EcoRI fragment of pFFT209 containing the complete chimeric construct (enh.35S+ALMV-fft-nos) was cloned into the HindIII and EcoRI site of pBINPLUS (Van Engelen et al., 1995), a binary plant transformation vector derived from pBIN19 (Bevan, 1984) resulting in plasmid pVF1 (FIG. 5B).

Example 4
Transformation of Petunia and potato plants

The binary vectors pVS1 and pVF1 (FIG. 5) were conjugated from *E. coli* XL1-Blue to *Agrobacterium tumefaciens* strain AGLO by triparental mating (Ditta et al., 1980). Exconjugants were used to transform *Petunia hybrida* leaf discs as described by Horsch et al. (1985). Leaf discs were prepared from top leaves of young non-flowering plants. *P. hybrida* variety W115 was used for the transformation experiments. Exconjugants were also used to transform diploid potato (*Solanum tuberosum,* variety Kardal) stem explants as described previously (Visser, 1991). After shoot and root regeneration on kanamycin-containing media, plants were put in soil and transferred to the greenhouse. Plants regenerated (on kanamycin-free media) from leaf discs and stem explants treated with the Agrobacterium strain AGLO lacking a binary vector served as a control.

Example 5
Analysis of transgenic plants expressing the sst and fft genes

About 25 transgenic petunia plants and 25 transgenic potato plants were generated harboring the pVS1 construct and 25 transgenic petunia and potato plants harboring the pVF1 construct. Ten petunia and ten potato plants were transformed with the Agrobacterium strain AGL0 lacking a binary vector. These plants were used as a control. Southern blot analysis of genomic DNA isolated from the transformed plants showed that on average 1–5 copies of the introduced chimeric genes were integrated (data not shown).

Figure 6:
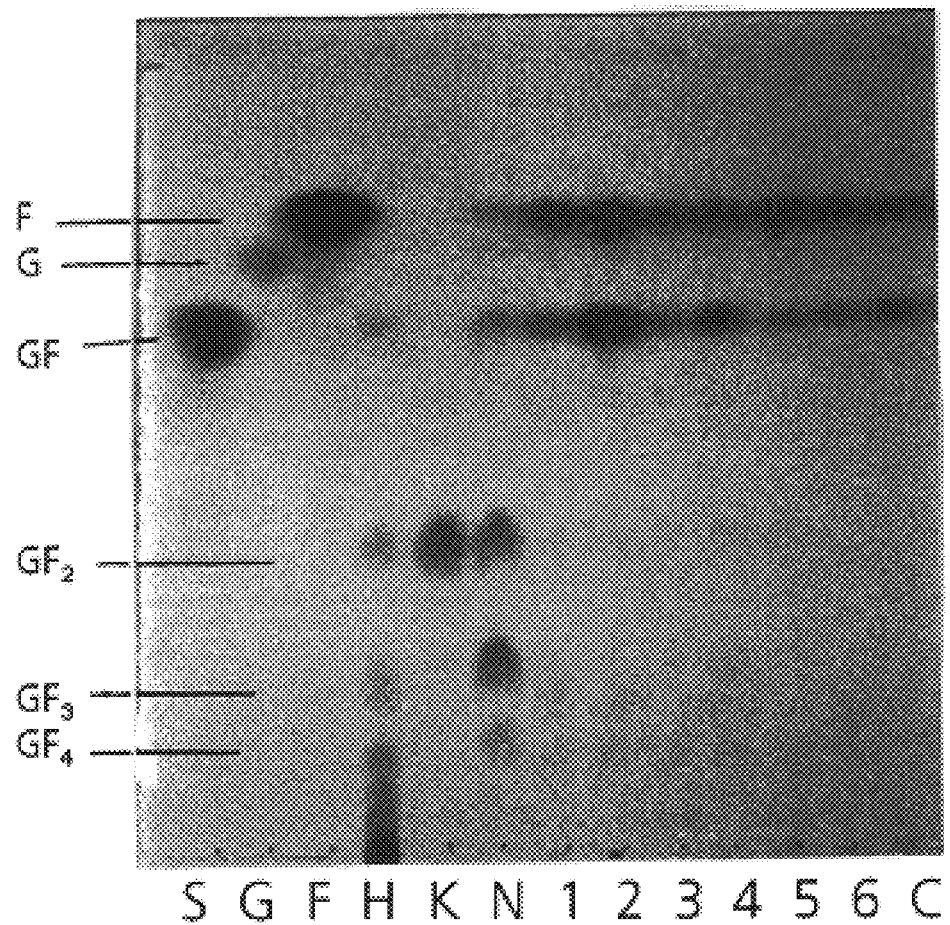
FIG. 6. TLC analysis of fructans in transgenic potato plants harboring the pSF1 construct. TLC plates were developed twice in 90% aqueous acetone. S=sucrose standard, G=glucose standard, F=fructose standard, H=standard fructan mixture from tubers of *H. tuberosus*, N=Neosugar standard, K=G-(F)$_2$-standard. No. 1–6 represent individual potato plants harboring the pVS1 construct. C is control plant harboring the AGL0 construct.
Figure 7:
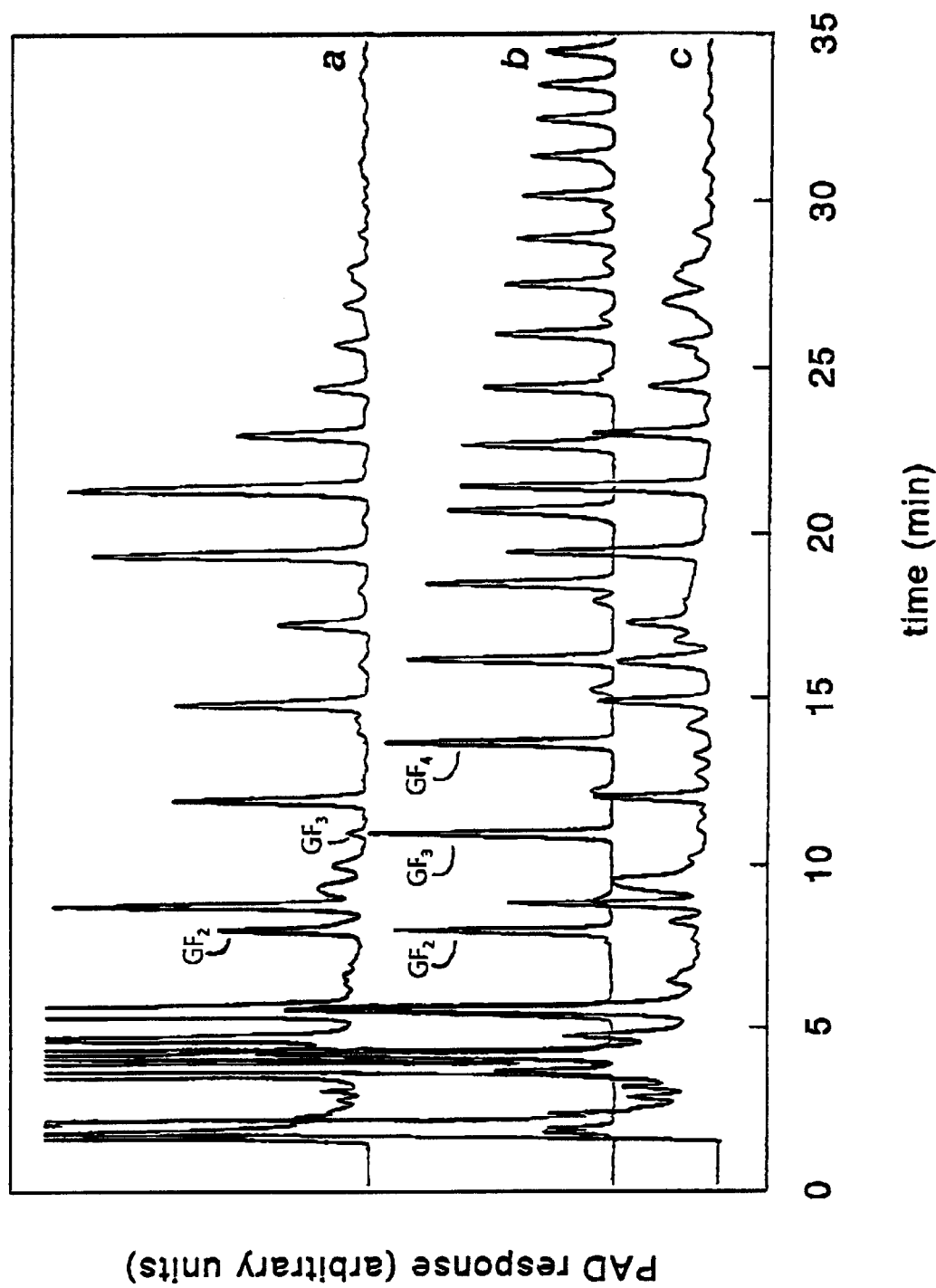
FIG. 7. HPAEC separations of carbohydrates extracted from leaves of *Petunia hybrida* harboring the pVS1 construct (a), a standard fructan mixture extracted from *H. tuberosus* tubers (b), and carbohydrates from leaves of the control Petunia harboring the AGL0 construct (c).
Figure 8:
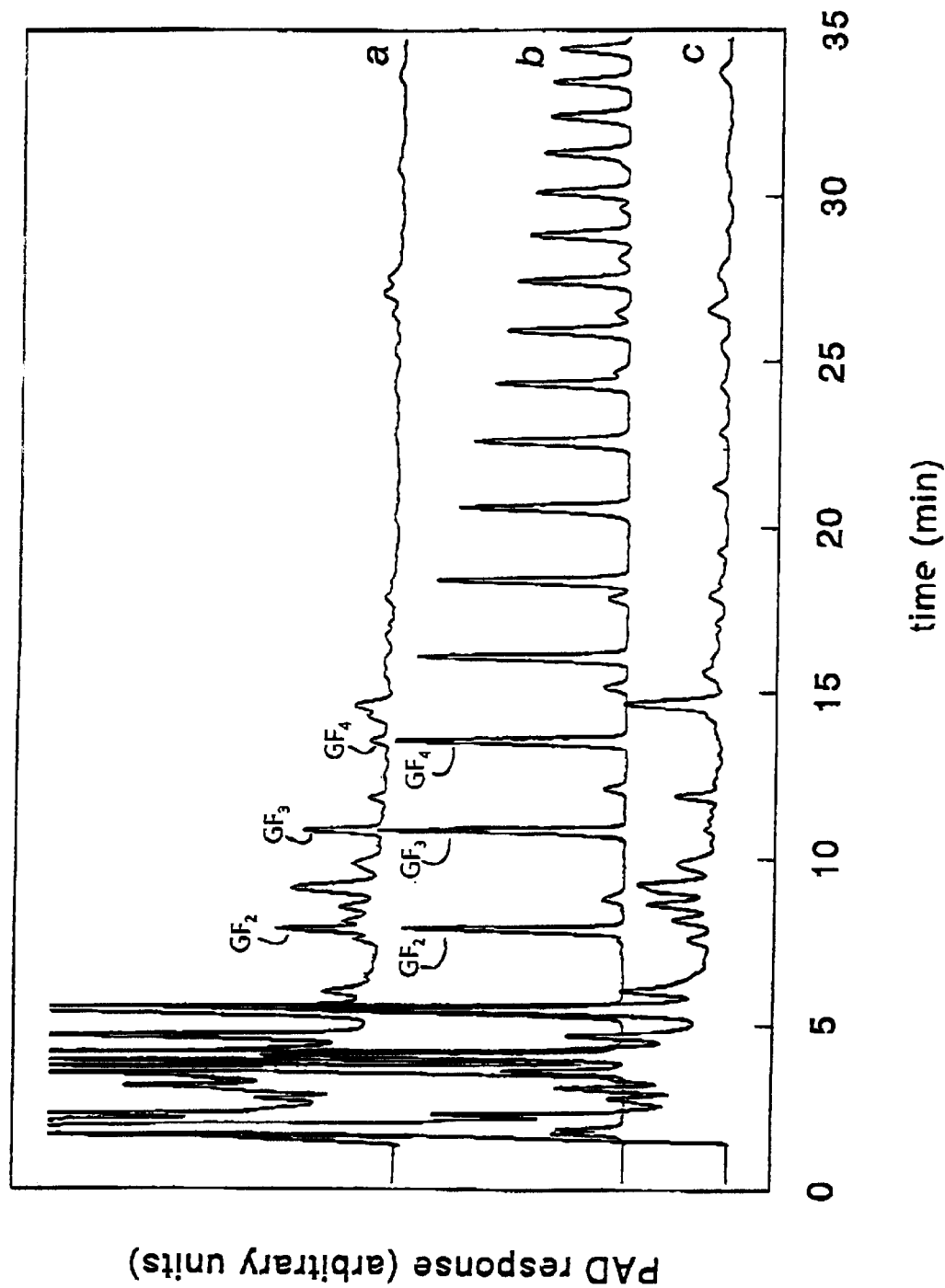
FIG. 8. HPAEC separations of carbohydrates extracted from leaves of potato (*Solanum tuberosum*) harboring the pVS1 construct (a), a standard fructan mixture extracted from *H. tuberosus* tubers (b), and carbohydrates from leaves of the control potato harboring the AGL0 construct (c).

The carbohydrate composition of transgenic plants was analysed by two essentially different techniques: thin layer chromatography (TLC), which separate carbohydrates on basis of liquid—liquid partitioning (after TLC, the fructans were detected by a fructose specific colour reaction) and HPAEC, which separate carbohydrates at alkaline conditions (pH 13) on basis of charge, and detect carbohydrates by oxidation with a gold working electrode. Analysis of leaves extracts from the potato and Petunia plants harboring the pVS1 construct showed that both transgenic plant species contain products which are the result of SST activity. TLC showed the presence of at least the trisaccharide $G\text{-}(F)_2$ and most probably also the tetrasaccharide $G\text{-}(F)_3$ and the pentasaccharide $G\text{-}(F)_4$ in extracts of potato leaves, whereas these oligofructans were absent in the control plant (FIG. 6). The presence of $G\text{-}(F)_2$ and $G\text{-}(F)_3$ in leave extracts of potato but also of transgenic *P. hybrida* plants was demonstrated by HPAE analysis (FIGS. 7 and 8). HPAEC, which is more sensitive and more specific than TLC, also revealed a small amount of $G\text{-}(F)_4$ in transgenic potato (FIG. 8). The results of FIGS. 6–8 clearly indicate that the sst gene is expressed into an enzymatically active SST protein in both *P. hybrida* and potato.

Transgenic plants harboring the pVF1 construct did not contain fructans because FFT needs oligofructans (such as $G\text{-}(F)_2$ or $G\text{-}(F)_3$) as initial substrates for the synthesis of fructans. Oligofructans are not present in plants lacking SST activity such as wild type potato or Petunia, or transgenic plants only containing the pVF1 construct. The presence of FFT activity in transgenic plants harboring the pVF1 construct is therefore verified by FFT activity measurements.

Figure 9:
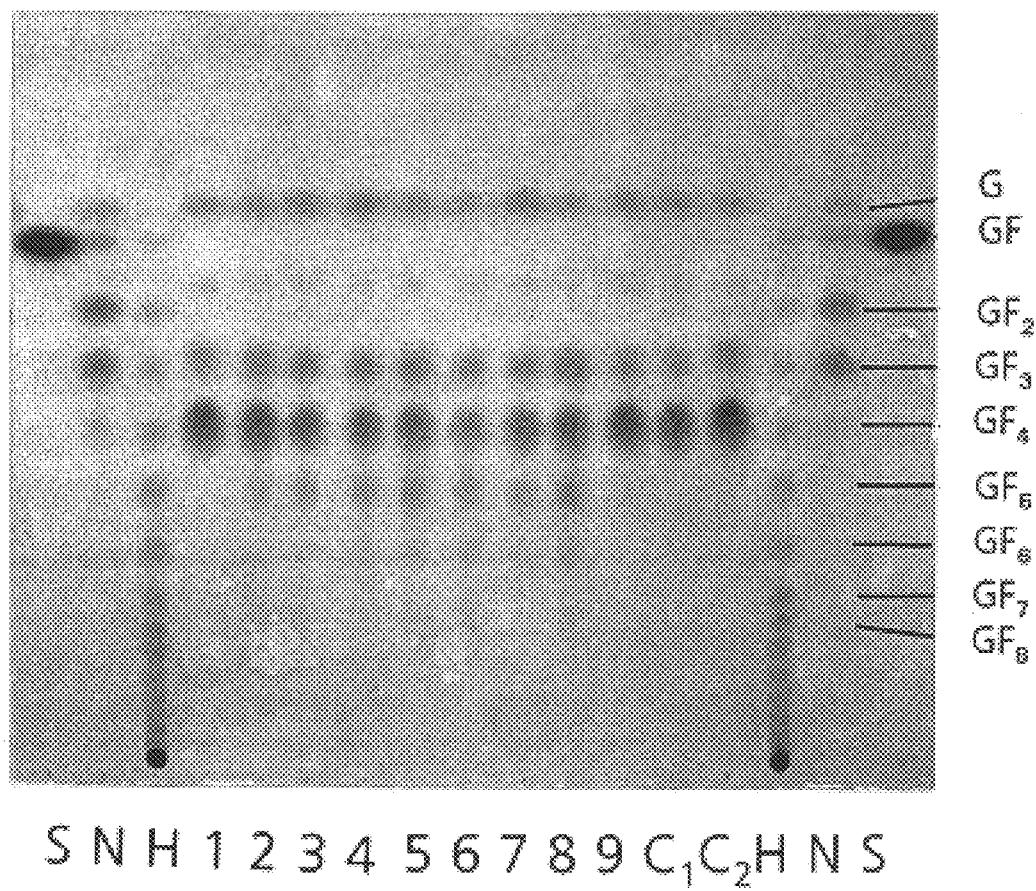
FIG. 9. TLC analysis of fructans synthesized from G-(F)$_4$ by protein extracts from leaves of transgenic potato plants harboring the pVF1 construct. TLC plates were developed twice in butan-1-ol, propan-2-ol and water (3:12:4, v/v). S=sucrose standard; N=Neosugar standard, H=standard fructan mixture from tubers of *H. tuberosus*. No. 1–8 represent different individual transgenic potato plants harboring the pVF1 construct. C$_1$ and C$_2$ are control plants harboring the AGL0 construct.

The FFT assay used to evaluate the presence of an active FFT in transgenic potato was based on the ability of FFT to catalyse the synthesis of $G\text{-}(F)_n$, n>4, at the expense of $G\text{-}(F)_4$. The total leaf protein extract from potato plants harboring the pVF1 construct, was mixed with an $G\text{-}(F)_4$ containing assay mixture, and the presence of fructans with a higher degree of polymerization ($G\text{-}(F)_n$, n>4) was examined by TLC. Already after 4 h of incubation, $G\text{-}(F)_5$ and $G\text{-}(F)_6$ could be detected. After 44 h of incubation, fructans with a degree of polymerization higher then 4, including $G\text{-}(F)_4$, $G\text{-}(F)_5$, $G\text{-}(F)_6$, $G\text{-}(F)_7$ and $G\text{-}(F)_8$, could be detected, whereas these fructans were absent in the control mixtures (FIG. 9). This indicates that also the fft gene is expressed into an enzymatically active FFT protein.

DEFINITIONS AND ABBREVIATIONS

Fructan nomenclature is as according to Lewis (1993)

Fructosyl unit: a fructose molecule linked to another sugar molecule (e.g. glucose, fructose or galactose). Abbreviated as -F (e.g. in G-F) or -F-(e.g. G-F-F). For molecules consisting of more then one fructosyl unit (e.g. G-F-F-F-F) a condensed notation is used $[G\text{-}(F)_6]$ or $GF_6$. $G\text{-}(F)_6$ consists of one glucosyl and 6 fructosyl units. $G\text{-}(F)_6$ consists of one fructosyl-glucose linkage and 5 fructosyl-fructose linkages.

Oligofructans: Any compound with one, two, or three fructosyl-fructose linkages (a glucose may be present but is not necessary). In the present application, the term oligofructans was used to denote the products of SST-activity $[G\text{-}(F)_2, G\text{-}(F)_3 \text{ and } G\text{-}(F)_4]$. Oligofructans are more generally denoted as short chain fructans or fructans with a low degree of polymerization. In the present application oligofructans also include compounds consisting of 2, 3 or 4 fructosyl units, but lacking the glucosyl unit.

Fructans: Any compound in which one or more fructosyl-fructose linkages constitute a majority of the linkages (a glucose may be present but is not necessary). Fructan is used as a numerative noun where the materials referred to are chemically distinct (e.g. the fructans $G\text{-}(F)_2$ and $G\text{-}(F)_{13}$. In the present application, fructans are defined as the products of FFT activity ($G\text{-}F_n$, $2 \leq n < \pm 60$). Unless indicated otherwise, fructans include also oligofructans. To denote a restricted group of fructans the "$G\text{-}F_n$, n= . . . " notation is used. In the present application fructans also include compounds consisting of more than 1 fructosyl unit, but lacking the glucosyl unit.

Inulin: Fructan that has mostly the β-2,1-fructosyl-fructose linkage (a glucose may be present, but not is necessary). Cumulative vs. numerative usage as a noun is the same as for fructan above.

Levan: Fructan that has mostly the β-2,1-fructosyl-fructose linkage (a glucose is allowed but not necessary). Levan is also used to denote fructans from bacterial origin, although bacterial fructans do not always consists of predominantly β-2,6 fructosyl-fructose linkages. For example, the fructans synthesized by levansucrase from *Bacillus subtilus* have predominantly β-2,1-fructosyl-fructose linkages (inulin). Cumulative vs. numerative usage of levan as a noun is the same as for fructan.

Levansucrase: Enzymes from bacterial origin that are involved in the synthesis of fructan.

Sucrose:sucrose fructosyltransferase (SST): Plant-derived enzyme catalyzing the initial step of fructan synthesis (reaction 2). Enzyme can also be involved in the synthesis of oligofructans $[G\text{-}(F)_n, 2 \leq n \leq 4]$ (reaction 3). In the present application, the designation SST can include either 1-SST, an SST form involved in the biosynthesis of oligofructans that has mostly the β-2,1-fructosyl-fructose linkage; or 6-SST, an SST form involved in the biosynthesis of oligofructans that has mostly the β-2,6-fructosyl-fructose linkage; or 1-SST and 6-SST.

Fructan:fructan fructosyltransferase (FFT). Plant-derived enzyme involved in the synthesis of fructans. Enzyme capable of catalyzing the synthesis of oligofructans and fructans of a higher degree of polymerization. FFT from *H. tuberosus* has overlapping activity with SST from *H. tuberosus* (reaction 3), but cannot catalyse the initial step of fructan synthesis (reaction 2). In the present application, the designation FFT can include either 1-FFT, an FFT form involved in the biosynthesis of oligofructans that has mostly the β-2,1-fructosyl-fructose linkage; or 6-FFT, an FFT form involved in the biosynthesis of fructans that has mostly the β-2,6-fructosyl-fructose linkage; or 1-FFT and 6-FFT.

Invertase: β-fructosidase or β-fructofuranosidase.

Degree of polymerization (DP): term to indicate the total amount of fructosyl and glycosyl residues; for example, $G\text{-}(F)_2$ has a DP of 3. The n-value in $G\text{-}F_n$ increases with an increasing degree of polymerization.

Fructan profile: term to describe the fructan size/distribution pattern, or alternatively, the relative amounts and kinds of fructans, in an extract for example derived from a plant, plant organ or plant cell. The currently most reliable method to analyze a fructran pattern of an extract is by high performance anion exchange chromatography and pulsed amperometric detection (Chatterton et al. 1990).

*Helianthus tuberosus*: Jerusalem artichoke.

*Cichorium intybus*: chicory.

HPLC: High Performance Liquid Chromatography. Technique for the separation of complex mixtures of compounds. Variants on this technique are high performance reversed phase chromatography (RP HPLC) or high performance anion exchange chromatography in combination with pulsed amperometric detection (HPAEC-PAD, see for example FIG. 3).

REFERENCES

Angenent G C, Ebskamp M J M, Weisbeek P J and Smeekens S C M. (1993). Purification and properties of sucrose—sucrose fructosyltransferases in barley leaves and onion seeds. In: Fuchs A, ed. Inulin ans inulin containing crops. Elsevier, Amsterdam, the Netherlands, pp. 173–184.

Ausubel F M, Brent R, Kingston R E, Moore D D, Seidman J G, Smith J A, and Struhl K. (1994). Current protocols in molecular biology. John Wiley & Sons.

Bevan M. (1984). Binary Agrobacterium vectors for plant transformation. Nucleic Acids Research 12, 8711–8721.

Carlsson J. (1970). A levansucrase from *Streptococcus mutans*. Caries Research 4, 97–113

Chatterton N J, Harrison P A, Thornley W R, Draper E A. 1990. Oligosaccharides in foliage of Agropyron, Bromus, Dactylis, Festuca, Lolium, and Phleum. New Phytologist 114, 167–171.

Darwen C W E, John P. (1989). Localization of the enzymes of fructan metabolism in vacuoles isolated by a mechanical method from tubers of Jerusalem artichoke (*Helianthus tuberosus* L.). Plant Physiology 89, 658–663.

Dedonder R. (1966). Levansucrase from *Bacillus subtilus*. Methods in Enzymology 8, 500–505.

Ditta G, Stanfield S, Corbi D. and Helinski D R (1980). Broad host range DNA cloning system for Gram-negative bacteria: Construction of a gene bank of *Rhizobium meliloti*. Proceedings National Academy Science USA 77, 7347–7351.

Ebskamp M J M, van der Meer I M, Spronk B A, Weisbeek P J and Smeekens J C M (1994). Accumulation of fructose polymers in transgenic tabacco. Bio/Technology 12, 272–275.

Heinze B and Praznik W. (1991). Separation and purification of inulin oligomers and polymers by reversed-phase high-performance liquid chromatography. Journal of Applied Polymer Science: Applied Polymer Symposium 48, 207–225.

Horsch R B, Fry J E, Hoffman N L, Eichholtz D, Rogers S G, and Fraley R T. (1968). A simple and general method for transferring genes into plants. Science 227, 1229–1232.

Jacques N A. (1993). The fructosyltransferase of *Streptococcus salivarius*. New Phytologist 123, 429–435.

Koops A J and Jonker H H (1994). Purification and characterization of the enzymes of fructan biosynthesis in tubers of *Helianthus tuberosus* 'Colombia,' I. Fructan:fructran fructosyltransferase. Journal of Experimental Botany 45, 1623–1631

Laemmli U K. (1970). Cleavage of structural proteins during assembly of the head of bacteriophage T4. Nature 227, 680–685.

Lewis D H. (1993). Nomenclature and diagrammatic representation of oligomeric fructans—a paper for discussion New Phytologist. 124, 583–594.

Lüscher M, Prehner M, Nösberger J. (1993). Purification and characterization of fructan:fructan fructosyltransferase from Jerusalem artichoke (*Helianthus tuberosus* L.). New Phytologist 123, 717–24.

Meier H, Reid J S G. (1982). Reserve polysaccharides other than starch in higher plants. In: Loewus F A, Tanner W, eds. Encyclopedia of Plant Physiology, New Series 13. Berlin-Springer Verlag, 1418–71.

Pen J, Molendijk L, Quax W J, Sijmons P C, van. Ooyen A J J, van den Elzen P J M, Rietveld R. and Hoekema A. (1992). Production of active *Bacillus licheniformis* alpha-amylase in tobacco and its application in starch liquefaction. Bio/Technology 10, 292–296.

Praznik W. Beck R H F and Spies Th. (1990), Isolation and characterization of sucrose:sucrose $1^F$-β-D-fructosyltransferase from tubers of *Helianthus tuberosis*, L. Agric. biol. Chem. 54, 2429–2431.

Rosenfeld J, Capdevielle J, Guillemot J C, Ferrara P. (1992). In-gel digestion or proteins for internal sequence analysis after one- or two-dimensional gel electrophoresis. Analytical Biochemistry 203, 173–179.

Sambrook J. Fritsch E F, Maniatis T. (1989) Molecular cloning. A laboratory manual. Cold Spring Harbor Laboratory Press, Cold Spring Harbor.

Sato S, Kuramitsu H K, (1986). Isolation and characterization of a fructosyltransferase gene from *Streptococcus murans* GS-5. Infect. Immun 52, 166–170.

Shiomi N and Izawa M. (1980). Purification and characterization of sucrose:sucrose 1-fructosyltransferase from roots of asparagus (*Asparagus officinalis* L.). Agric. Biol. Chem. 44, 603–614.

Steinmetz M, Le Coq D, Aymerich S, Gonzy Treboul G, Gay P. (1985). The DNA sequence of the gene for the secreted *Bacillus subtilus* enzyme levansucrase and its genetic control sites. Molecular & General Genetics 200, 220–228.

Van der Meer I M, Ebskamp M J M, Visser R G F, Weisbeek P J and Smeekens J C M. (1994). Fructan as a new carbohydrate sink in transgenic potato plants. Plant Cell 6, 561–570.

Van Engelen F A, Molthoff J W, Conner, A J, Nap J-P, Pereira A, and Stiekema W J. (1995). pBINPLUS: an improved plant transformation vector based on pBIN19. Transgenic Research 4, 288–290.

Vissex R G F. (1991). Regeneration and transformation of potato by *Agrobacterium tumefaciens*. In: *Plant Tissue Culture Manual B5*, edited by Lindsey, K. Dordrecht, The Netherlands, Kluwer Academic Publishers, pp. 1–9.

Wagner W, Keller F, Wiemken. (1983). Fructan metabolism in cereals: induction in leaves and compartmentation in protoplasts and vacuoles. Zeitschrift für Pflanzenphysiologie 112, 359–372.

Wise C S, Dimler R J, Davi9s H A, Rist C E. 1955. Determination of easily hydrolysable fructose units in dextran preparations. Analytical Chemistry 27, 33–6.

What is claimed is:

1. An isolated DNA fragment having a nucleotide sequence SEQ ID NO. 1 as shown in FIG. 4A or a homologous sequence having a similarity of at least 70% with SEQ ID NO. 1, said homologous sequence encoding a protein having 1-sucrose:sucrose fructosyltransferase activity, said protein catalyses the reaction; $G\text{-}(F)_n + G\text{-}(F)_m \rightarrow G\text{-}(F)_{n-1} + G\text{-}(F)_{m+1}$, $1 < n < 3$, $1 \leq m \leq 3$ wherein G represents a glucosyl unit and -F represents a fructosyl unit.

2. An isolated DNA fragment having a nucleotide sequence SEQ ID NO. 3 as shown in FIG. 4B or a homologous sequence having a similarity of at least 70% with SEQ ID NO. 3, said homologous sequence encoding a protein having 1-fructan:fructan fructosyltransferase activity, said protein catalyses the reaction: $G\text{-}(F)_n + G\text{-}(F)_m \rightarrow G\text{-}(F)_{n-1} + G\text{-}(F)_{m+1}$, $n \geq 2$, $m \geq 2$ wherein-G represents a glucosyl unit and F represents a fructosyl unit.

3. An isolated DNA fragment according to claim 1 having a sequence with a similarity of at least 85% with SEQ ID NO. 1, said sequence encoding a protein having 1-sucrose:sucrose fructosyltransferase activity, said protein catalyses the reaction: $G\text{-}(F)_n + G\text{-}(F)_m \rightarrow G\text{-}(F)_{n-1} + G\text{-}(F)_{m+1}$, $1 \leq n \leq 3$, $1 \leq m \leq 3$ wherein -G represents a glucosyl unit and -F represents a fructosyl unit.

4. A recombinant DNA sequence comprising one or more DNA fragments as defined in claim 1.

5. A method for producing a genetically transformed microbial or plant host showing a modified fructan profile, which comprises the steps of:
   i) preparing a chimeric gene construct comprising one or more DNA fragments as defined in claim 1, operably linked to a promoter sequence active in said host and
   ii) introducing the chimeric gene construct into the genome of the host.

6. A method according to claim 5, wherein said host is a plant, and the method additionally comprises the step of iii) regenerating the transformed plant cells to transgenic plants.

7. A transformed plant produced by the method of claim 6, or a plant cell, seed, fruit, seedling or any plant part comprising said chimeric gene construct.

8. An isolated DNA fragment according to claim 2 having a sequence with a similarity of at least 85% with SEQ ID NO. 3, said sequence fragment encoding 1-fructan:fructan fructosyltransferase.

9. A recombinant DNA sequence comprising one or more DNA fragments as defined in claim 2.

10. A method for producing a genetically transformed microbial or plant host showing a modified fructan profile, which comprises the steps of:
    i) preparing a chimeric gene construct comprising one or more DNA fragments as defined in claim 1 and one or more DNA fragments as defined in claim 2, operably linked to a promoter sequence active in said host and a terminator sequence active in said host, and
    ii) introducing the chimeric gene construct into the genome of a cell of the host.

11. A method according to claim 10, wherein said host is a plant, and the method additionally comprises the step of iii) regenerating the transformed plant cells to transgenic plants.

12. A transformed plant produced by the method of claim 11, or a plant cell, seed, fruit, seedling or any plant part comprising said chimeric gene construct.

13. A method for producing a genetically transformed microbial or plant host showing a modified fructan profile, which comprises the steps of:
    i) preparing a chimeric gene construct comprising one or more DNA fragments as defined in claim 2 and one or more DNA fragments encoding 1-sucrose:sucrose fructosyltransferase, operably linked to a promoter sequence active in said host and a terminator sequence active in said host organism, and
    ii) introducing the chimeric gene construct into the genome of a cell of the host.

14. A method according to claim 13, wherein said host is a plant, and the method additionally comprises the step of iii) regenerating the transformed plant cells to transgenic plants.

15. A transformed plant produced by the method of claim 14, or a plant cell, seed, fruit, seedling or any plant part comprising said chimeric gene construct.

16. A method according for producing a genetically transformed microbial or plant host showing a modified fructan profile, which comprises the steps of:
    i) preparing a chimeric gene construct comprising one or more DNA fragments as defined in claim 2, operably linked to a promoter sequence active in said host, and a terminator sequence active in said host, and
    ii) introducing the chimeric gene construct into the genome of a cell of the host comprising one or more DNA fragments encoding 1-sucrose:sucrose fructosyltransferase and one or more DNA fragments encoding 1-fructan:fructan fructosyltransferase.

17. A method according to claim 16, wherein said host is a plant, and the method additionally comprises the step of iii) regenerating the transformed plant cells to transgenic plants.

18. A transformed plant produced by the method of claim 17, or a plant cell, seed, fruit, seedling or any plant part comprising said chimeric gene construct.

19. A recombinant DNA sequence comprising one or more DNA fragments as defined in claim 3.

20. A method for producing a genetically transformed microbial or plant host showing a modified fructan profile, which comprises the steps of:
   i) preparing a chimeric gene construct comprising one or more DNA fragments as defined in claim 3, operably linked to a promoter sequence active in said host, and a terminator sequence active in said host, and
   ii) introducing the chimeric gene construct into the genome of a cell of the host.

21. A method according to claim 20, wherein said host is a plant, and the method additionally comprises the step of iii) regenerating the transformed plant cells to transgenic plants.

22. A transformed plant produced by the method of claim 21, or a plant cell, seed, fruit, seedling or any plant part comprising said chimeric gene construct.

23. A recombinant DNA sequence comprising one or more DNA fragments as defined in claim 8.

24. A method for producing a genetically transformed microbial or plant host showing a modified fructan profile, which comprises the steps of:
   i) preparing a chimeric gene construct comprising one or more DNA fragments as defined in claim 8, operably linked to a promoter sequence active in said host organism and a terminator sequence active in said host, and
   ii) introducing the chimeric gene construct into the genome of a cell of the host.

25. A method according to claim 24, wherein said host is a plant, and the method additionally comprises the step of iii) regenerating the transformed plant cells to transgenic plants.

26. A transformed plant produced by the method of claim 25, or a plant cell, seed, fruit, seedling or any plant part comprising said chimeric gene construct.

* * * * *

```
                              SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
         (A) LENGTH: 2116 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Helianthus tuberosus
         (B) STRAIN: Columbia
         (D) DEVELOPMENTAL STAGE: Adult
         (F) TISSUE TYPE: Tuber
         (G) CELL TYPE: storage parenchyma (vii) IMMEDIATE SOURCE:
         (A) LIBRARY: lambda Uni-Zap XR (Stratagene, USA)
         (B) CLONE: pSST103

(ix) FEATURE:
         (A) NAME/KEY: CDS
         (B) LOCATION:34..1923

(x) PUBLICATION INFORMATION:
         (H) DOCUMENT NUMBER: WO 89/12386 A1
         (I) FILING DATE: 21-JUN-1989
         (J) PUBLICATION DATE: 28-DEC-1989
         (K) RELEVANT RESIDUES IN SEQ ID NO: 1: FROM 1 TO 4100

(x) PUBLICATION INFORMATION:
         (H) DOCUMENT NUMBER: WO 94/04692 A1
         (I) FILING DATE: 09-AUG-1993
         (J) PUBLICATION DATE: 03-MAR-1994
         (K) RELEVANT RESIDUES IN SEQ ID NO: 1: FROM 1 TO 1438

(x) PUBLICATION INFORMATION:
         (H) DOCUMENT NUMBER: WO 94/14970 A1
         (I) FILING DATE: 28-DEC-1993
         (J) PUBLICATION DATE: 07-JUL-1994

(xi) SEQUENCE DESCRIPTION: SEQ ID NO: 1:

GGCACGAGAA AAAACCCTCC CTCAGGCCAC CAC ATG ATG GCT TCA TCC ACC ACC          54
                                     Met Met Ala Ser Ser Thr Thr
                                       1               5

ACC ACC CCT CTC ATT CTC CAT GAT GAC CCT GAA AAC CTC CCA GAA CTC          102
Thr Thr Pro Leu Ile Leu His Asp Asp Pro Glu Asn Leu Pro Glu Leu
         10              15                  20

ACC GGT TCT CCG ACA ACT CGT CGT CTA TCC ATC GCA AAA GTG CTT TCG          150
Thr Gly Ser Pro Thr Thr Arg Arg Leu Ser Ile Ala Lys Val Leu Ser
     25                  30                  35
```

```
GGG ATC CTT GTT TCG GTT CTG GTT ATA GGT GCT CTT GTT GCT TTA ATC      198
Gly Ile Leu Val Ser Val Leu Val Ile Gly Ala Leu Val Ala Leu Ile
 40              45                  50                  55

AAC AAC CAA ACA TAT GAA TCC CCC TCG GCC ACC ACA TTC GTA ACT CAG      246
Asn Asn Gln Thr Tyr Glu Ser Pro Ser Ala Thr Thr Phe Val Thr Gln
                 60                  65                  70

TTG CCA AAT ATT GAT CTG AAG CGG GTT CCA GGA AAG TTG GAT TCG AGT      294
Leu Pro Asn Ile Asp Leu Lys Arg Val Pro Gly Lys Leu Asp Ser Ser
             75                  80                  85

GCT GAG GTT GAA TGG CAA CGA TCC ACT TAT CAT TTT CAA CCC GAC AAA      342
Ala Glu Val Glu Trp Gln Arg Ser Thr Tyr His Phe Gln Pro Asp Lys
         90                  95                 100

AAT TTC ATT AGC GAT CCT GAT GGC CCA ATG TAT CAC ATG GGA TGG TAT      390
Asn Phe Ile Ser Asp Pro Asp Gly Pro Met Tyr His Met Gly Trp Tyr
    105                 110                 115

CAT CTA TTT TAT CAG TAC AAC CCT CAA TCT GCC ATC TGG GGC AAC ATC      438
His Leu Phe Tyr Gln Tyr Asn Pro Gln Ser Ala Ile Trp Gly Asn Ile
120                 125                 130                 135

ACA TGG GGC CAC TCG GTA TCG AAA GAC ATG ATC AAC TGG TTC CAT CTC      486
Thr Trp Gly His Ser Val Ser Lys Asp Met Ile Asn Trp Phe His Leu
                140                 145                 150

CCT TTC GCC ATG GTT CCT GAC CAT TGG TAC GAC ATC GAA GGT GTC ATG      534
Pro Phe Ala Met Val Pro Asp His Trp Tyr Asp Ile Glu Gly Val Met
            155                 160                 165

ACG GGT TCG GCT ACA GTC CTC CCT AAT GGT CAA ATC ATC ATG CTT TAC      582
Thr Gly Ser Ala Thr Val Leu Pro Asn Gly Gln Ile Ile Met Leu Tyr
        170                 175                 180

TCG GGC AAC GCG TAT GAT CTC TCC CAA GTA CAA TGC TTG GCG TAC GCT      630
Ser Gly Asn Ala Tyr Asp Leu Ser Gln Val Gln Cys Leu Ala Tyr Ala
    185                 190                 195

GTC AAC TCG TCG GAT CCA CTT CTT ATA GAG TGG AAA AAA TAT GAA GGT      678
Val Asn Ser Ser Asp Pro Leu Leu Ile Glu Trp Lys Lys Tyr Glu Gly
200                 205                 210                 215

AAC CCT GTC TTA CTC CCA CCA CCA GGA GTA GGC TAC AAG GAC TTT CGG      726
Asn Pro Val Leu Leu Pro Pro Pro Gly Val Gly Tyr Lys Asp Phe Arg
                220                 225                 230

GAC CCA TCC ACA TTG TGG TCG GGC CCT GAT GGT GAA TAT AGA ATG GTA      774
Asp Pro Ser Thr Leu Trp Ser Gly Pro Asp Gly Glu Tyr Arg Met Val
            235                 240                 245

ATG GGG TCC AAG CAC AAC GAG ACT ATT GGC TGT GCT TTG ATT TAC CAT      822
Met Gly Ser Lys His Asn Glu Thr Ile Gly Cys Ala Leu Ile Tyr His
        250                 255                 260

ACC ACT AAT TTT ACG CAT TTT GAA TTG AAA GAG GAG GTG CTT CAT GCA      870
Thr Thr Asn Phe Thr His Phe Glu Leu Lys Glu Glu Val Leu His Ala
    265                 270                 275

GTC CCA CAT ACT GGT ATG TGG GAA TGT GTT GAT CTT TAC CCG GTG TCC      918
Val Pro His Thr Gly Met Trp Glu Cys Val Asp Leu Tyr Pro Val Ser
280                 285                 290                 295

ACC GTA CAC ACA AAC GGG CTG GAC ATG GTG GAT AAC GGG CCA AAT GTT      966
Thr Val His Thr Asn Gly Leu Asp Met Val Asp Asn Gly Pro Asn Val
                300                 305                 310

AAG TAC GTG TTG AAA CAA AGT GGG GAT GAA GAT CGC CAT GAT TGG TAT     1014
Lys Tyr Val Leu Lys Gln Ser Gly Asp Glu Asp Arg His Asp Trp Tyr
            315                 320                 325

GCA ATT GGA AGT TAC GAT ATA GTG AAT GAT AAG TGG TAC CCA GAT GAC     1062
Ala Ile Gly Ser Tyr Asp Ile Val Asn Asp Lys Trp Tyr Pro Asp Asp
        330                 335                 340

CCG GAA AAT GAT GTG GGT ATC GGA TTA AGA TAT GAT TTT GGA AAA TTT     1110
Pro Glu Asn Asp Val Gly Ile Gly Leu Arg Tyr Asp Phe Gly Lys Phe
    345                 350                 355
```

-continued

```
TAT GCG TCC AAG ACG TTT TAT GAC CAA CAT AAG AAG AGG AGA GTC CTT    1158
Tyr Ala Ser Lys Thr Phe Tyr Asp Gln His Lys Lys Arg Arg Val Leu
360                 365                 370                 375

TGG GGC TAT GTT GGA GAA ACC GAT CCC CAA AAG TAT GAC CTT TCA AAG    1206
Trp Gly Tyr Val Gly Glu Thr Asp Pro Gln Lys Tyr Asp Leu Ser Lys
                380                 385                 390

GGA TGG GCT AAC ATT TTG AAT ATT CCA AGG ACC GTC GTT TTG GAC CTC    1254
Gly Trp Ala Asn Ile Leu Asn Ile Pro Arg Thr Val Val Leu Asp Leu
            395                 400                 405

GAA ACT AAA ACC AAT TTG ATT CAA TGG CCA ATC GAG GAA ACC GAA AAC    1302
Glu Thr Lys Thr Asn Leu Ile Gln Trp Pro Ile Glu Glu Thr Glu Asn
        410                 415                 420

CTT AGG TCG AAA AAG TAT GAT GAA TTT AAA GAC GTC GAG CTT CGA CCC    1350
Leu Arg Ser Lys Lys Tyr Asp Glu Phe Lys Asp Val Glu Leu Arg Pro
    425                 430                 435

GGG GCA CTC GTT CCC CTT GAG ATA GGC ACA GCC ACA CAG TTG GAT ATA    1398
Gly Ala Leu Val Pro Leu Glu Ile Gly Thr Ala Thr Gln Leu Asp Ile
440                 445                 450                 455

GTT GCG ACA TTC GAA ATC GAC CAA AAG ATG TTG GAA TCA ACG CTA GAG    1446
Val Ala Thr Phe Glu Ile Asp Gln Lys Met Leu Glu Ser Thr Leu Glu
                460                 465                 470

GCC GAT GTT CTA TTC AAT TGC ACG ACT AGT GAA GGC TCG GTT GCA AGG    1494
Ala Asp Val Leu Phe Asn Cys Thr Thr Ser Glu Gly Ser Val Ala Arg
            475                 480                 485

AGT GTG TTG GGA CCG TTT GGT GTG GTG GTT CTA GCC GAT GCC CAG CGC    1542
Ser Val Leu Gly Pro Phe Gly Val Val Val Leu Ala Asp Ala Gln Arg
        490                 495                 500

TCC GAA CAA CTT CCT GTA TAC TTC TAT ATC GCA AAA GAT ATT GAT GGA    1590
Ser Glu Gln Leu Pro Val Tyr Phe Tyr Ile Ala Lys Asp Ile Asp Gly
    505                 510                 515

ACC TCA CGA ACT TAT TTT TGT GCC GAC GAA ACA AGA TCA TCC AAG GAT    1638
Thr Ser Arg Thr Tyr Phe Cys Ala Asp Glu Thr Arg Ser Ser Lys Asp
520                 525                 530                 535

GTA AGC GTA GGG AAA TGG GTG TAC GGA AGC AGT GTT CCT GTC CTC CCA    1686
Val Ser Val Gly Lys Trp Val Tyr Gly Ser Ser Val Pro Val Leu Pro
                540                 545                 550

GGC GAA AAG TAC AAT ATG AGG TTA TTG GTG GAT CAT TCG ATA GTA GAG    1734
Gly Glu Lys Tyr Asn Met Arg Leu Leu Val Asp His Ser Ile Val Glu
            555                 560                 565

GGA TTT GCA CAA AAC GGG AGA ACC GTG GTG ACA TCA AGA GTG TAT CCA    1782
Gly Phe Ala Gln Asn Gly Arg Thr Val Val Thr Ser Arg Val Tyr Pro
        570                 575                 580

ACA AAG GCG ATC TAC AAC GCT GCG AAG GTG TTT TTG TTC AAC AAC GCG    1830
Thr Lys Ala Ile Tyr Asn Ala Ala Lys Val Phe Leu Phe Asn Asn Ala
    585                 590                 595

ACT GGA ATC AGT GTG AAG GCG TCG ATC AAG ATC TGG AAG ATG GGG GAA    1878
Thr Gly Ile Ser Val Lys Ala Ser Ile Lys Ile Trp Lys Met Gly Glu
600                 605                 610                 615

GCA GAA CTC AAT CCT TTC CCT CTT CCT GGG TGG ACT TTC GAA CTT        1923
Ala Glu Leu Asn Pro Phe Pro Leu Pro Gly Trp Thr Phe Glu Leu
                620                 625                 630

TGATGGTTAT ATTTTGGACC CTATATATGT GTTATTATCA TGATGGTTAT ATTTTGGACC  1983

CTATATATGT GTTATTATCA TGAAGCATAA GTTTGGACTG GAGGGGGTAT TATTGTAATT  2043

TTATATGCAT GTTCTATTAC TTGTGAGGTT ATAGTATGTA ATTAAATTAT TATATACTAT  2103

ATCAATTTCT AAT                                                    2116
```

(2) INFORMATION FOR SEQ ID NO: 2:

(i) SEQUENCE CHARACTERISTICS:
    (A) LENGTH: 630 amino acids
    (B) TYPE: amino acid
    (D) TOPOLOGY: linear (ii) MOLECULE TYPE: protein (xi) SEQUENCE DESCRIPTION: SEQ ID NO: 2:

```
Met Met Ala Ser Ser Thr Thr Thr Pro Leu Ile Leu His Asp Asp
 1               5                  10                  15

Pro Glu Asn Leu Pro Glu Leu Thr Gly Ser Pro Thr Thr Arg Arg Leu
                20                  25                  30

Ser Ile Ala Lys Val Leu Ser Gly Ile Leu Val Ser Val Leu Val Ile
            35                  40                  45

Gly Ala Leu Val Ala Leu Ile Asn Asn Gln Thr Tyr Glu Ser Pro Ser
    50                  55                  60

Ala Thr Thr Phe Val Thr Gln Leu Pro Asn Ile Asp Leu Lys Arg Val
65                  70                  75                  80

Pro Gly Lys Leu Asp Ser Ser Ala Glu Val Glu Trp Gln Arg Ser Thr
                85                  90                  95

Tyr His Phe Gln Pro Asp Lys Asn Phe Ile Ser Asp Pro Asp Gly Pro
                100                 105                 110

Met Tyr His Met Gly Trp Tyr His Leu Phe Tyr Gln Tyr Asn Pro Gln
            115                 120                 125

Ser Ala Ile Trp Gly Asn Ile Thr Trp Gly His Ser Val Ser Lys Asp
    130                 135                 140

Met Ile Asn Trp Phe His Leu Pro Phe Ala Met Val Pro Asp His Trp
145                 150                 155                 160

Tyr Asp Ile Glu Gly Val Met Thr Gly Ser Ala Thr Val Leu Pro Asn
                165                 170                 175

Gly Gln Ile Ile Met Leu Tyr Ser Gly Asn Ala Tyr Asp Leu Ser Gln
                180                 185                 190

Val Gln Cys Leu Ala Tyr Ala Val Asn Ser Ser Asp Pro Leu Leu Ile
            195                 200                 205

Glu Trp Lys Lys Tyr Glu Gly Asn Pro Val Leu Leu Pro Pro Pro Gly
    210                 215                 220

Val Gly Tyr Lys Asp Phe Arg Asp Pro Ser Thr Leu Trp Ser Gly Pro
225                 230                 235                 240

Asp Gly Glu Tyr Arg Met Val Met Gly Ser Lys His Asn Glu Thr Ile
                245                 250                 255

Gly Cys Ala Leu Ile Tyr His Thr Thr Asn Phe Thr His Phe Glu Leu
            260                 265                 270

Lys Glu Glu Val Leu His Ala Val Pro His Thr Gly Met Trp Glu Cys
    275                 280                 285

Val Asp Leu Tyr Pro Val Ser Thr Val His Thr Asn Gly Leu Asp Met
290                 295                 300

Val Asp Asn Gly Pro Asn Val Lys Val Tyr Leu Lys Gln Ser Gly Asp
305                 310                 315                 320

Glu Asp Arg His Asp Trp Tyr Ala Ile Gly Ser Tyr Asp Ile Val Asn
                325                 330                 335

Asp Lys Trp Tyr Pro Asp Asp Pro Glu Asn Asp Val Gly Ile Gly Leu
            340                 345                 350

Arg Tyr Asp Phe Gly Lys Phe Tyr Ala Ser Lys Thr Phe Tyr Asp Gln
    355                 360                 365
```

-continued

```
His Lys Lys Arg Arg Val Leu Trp Gly Tyr Val Gly Glu Thr Asp Pro
    370                 375                 380

Gln Lys Tyr Asp Leu Ser Lys Gly Trp Ala Asn Ile Leu Asn Ile Pro
385                 390                 395                 400

Arg Thr Val Val Leu Asp Leu Glu Thr Lys Thr Asn Leu Ile Gln Trp
                405                 410                 415

Pro Ile Glu Glu Thr Glu Asn Leu Arg Ser Lys Lys Tyr Asp Glu Phe
            420                 425                 430

Lys Asp Val Glu Leu Arg Pro Gly Ala Leu Val Pro Leu Glu Ile Gly
            435                 440                 445

Thr Ala Thr Gln Leu Asp Ile Val Ala Thr Phe Glu Ile Asp Gln Lys
            450                 455                 460

Met Leu Glu Ser Thr Leu Glu Ala Asp Val Leu Phe Asn Cys Thr Thr
465                 470                 475                 480

Ser Glu Gly Ser Val Ala Arg Ser Val Leu Gly Pro Phe Gly Val Val
                485                 490                 495

Val Leu Ala Asp Ala Gln Arg Ser Glu Gln Leu Pro Val Tyr Phe Tyr
            500                 505                 510

Ile Ala Lys Asp Ile Asp Gly Thr Ser Arg Thr Tyr Phe Cys Ala Asp
            515                 520                 525

Glu Thr Arg Ser Ser Lys Asp Val Ser Val Gly Lys Trp Val Tyr Gly
    530                 535                 540

Ser Ser Val Pro Val Leu Pro Gly Glu Lys Tyr Asn Met Arg Leu Leu
545                 550                 555                 560

Val Asp His Ser Ile Val Glu Gly Phe Ala Gln Asn Gly Arg Thr Val
                565                 570                 575

Val Thr Ser Arg Val Tyr Pro Thr Lys Ala Ile Tyr Asn Ala Ala Lys
            580                 585                 590

Val Phe Leu Phe Asn Asn Ala Thr Gly Ile Ser Val Lys Ala Ser Ile
            595                 600                 605

Lys Ile Trp Lys Met Gly Glu Ala Glu Leu Asn Pro Phe Pro Leu Pro
610                 615                 620

Gly Trp Thr Phe Glu Leu
625                 630
```

(2) INFORMATION FOR SEQ ID NO: 3:

(i) SEQUENCE CHARACTERISTICS:
        (A) LENGTH: 2003 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Helianthus tuberosus
        (B) STRAIN: Columbia
          1
        (D) DEVELOPMENTAL STAGE: Adult
        (F) TISSUE TYPE: Tuber
        (G) CELL TYPE: storage parenchyma (vii) IMMEDIATE SOURCE:
        (A) LIBRARY: lambda Uni-Zap XR (Stratagene, USA)
        (B) CLONE: pFFT111

(ix) FEATURE:

(A) NAME/KEY: CDS
            (B) LOCATION:29..1873

(x) PUBLICATION INFORMATION:
            (H) DOCUMENT NUMBER: WO 89/12386 A1
            (I) FILING DATE: 21-JUN-1989
            (J) PUBLICATION DATE: 28-DEC-1989
            (K) RELEVANT RESIDUES IN SEQ ID NO: 3: FROM 1 TO 4100

(x) PUBLICATION INFORMATION:
            (H) DOCUMENT NUMBER: WO 94/04692 A1
            (I) FILING DATE: 09-AUG-1993
            (J) PUBLICATION DATE: 03-MAR-1994
            (K) RELEVANT RESIDUES IN SEQ ID NO: 3: FROM 1 TO 1438

(x) PUBLICATION INFORMATION:
            (H) DOCUMENT NUMBER: WO 94/14970 A1
            (I) FILING DATE: 28-DEC-1993
            (J) PUBLICATION DATE: 07-JUL-1994

(xi) SEQUENCE DESCRIPTION: SEQ ID NO: 3:

```
GGGACGAGTA CCAGTCCAGT CAGTCACC ATG CAA ACC CCT GAA CCC TTT ACA            52
                              Met Gln Thr Pro Glu Pro Phe Thr
                                              635

GAC CTT GAA CAT GAA CCC CAC ACA CCC CTA CTG GAC CAC CAC CAC AAC          100
Asp Leu Glu His Glu Pro His Thr Pro Leu Leu Asp His His His Asn
    640                 645                 650

CCA CCA CCA CAA ACC ACC ACA AAA CCT TTG TTC ACC AGG GTT GTG TCC          148
Pro Pro Pro Gln Thr Thr Thr Lys Pro Leu Phe Thr Arg Val Val Ser
655                 660                 665                 670

GGT GTC ACC TTT GTT TTA TTC TTC TTT GGT TTC GCT ATC GTA TTC ATT          196
Gly Val Thr Phe Val Leu Phe Phe Phe Gly Phe Ala Ile Val Phe Ile
                675                 680                 685

GTT CTC AAC CAA CAG AAT TCT TCT GTT CGT ATC GTC ACC AAT TCG GAG          244
Val Leu Asn Gln Gln Asn Ser Ser Val Arg Ile Val Thr Asn Ser Glu
            690                 695                 700

AAA TCT TTT ATA AGG TAT TCG CAG ACC GAT CGC TTG TCG TGG GAA CGG          292
Lys Ser Phe Ile Arg Tyr Ser Gln Thr Asp Arg Leu Ser Trp Glu Arg
        705                 710                 715

ACC GCT TTT CAT TTT CAG CCT GCC AAG AAT TTT ATT TAC GAT CCA GAT          340
Thr Ala Phe His Phe Gln Pro Ala Lys Asn Phe Ile Tyr Asp Pro Asp
    720                 725                 730

GGT CAG TTG TTT CAC ATG GGC TGG TAC CAT ATG TTC TAT CAA TAC AAC          388
Gly Gln Leu Phe His Met Gly Trp Tyr His Met Phe Tyr Gln Tyr Asn
735                 740                 745                 750

CCA TAC GCA CCG GTT TGG GGC AAT ATG TCA TGG GGT CAC TCA GTG TCC          436
Pro Tyr Ala Pro Val Trp Gly Asn Met Ser Trp Gly His Ser Val Ser
                755                 760                 765

AAA GAC ATG ATC AAC TGG TAC GAG CTG CCA GTC GCT ATG GTC CCG ACC          484
Lys Asp Met Ile Asn Trp Tyr Glu Leu Pro Val Ala Met Val Pro Thr
            770                 775                 780

GAA TGG TAT GAT ATC GAG GGC GTC TTA TCC GGG TCT ACC ACG GTC CTT          532
Glu Trp Tyr Asp Ile Glu Gly Val Leu Ser Gly Ser Thr Thr Val Leu
        785                 790                 795

CCA AAC GGT CAG ATC TTT GCA TTG TAT ACT GGG AAC GCT AAT GAT TTT          580
Pro Asn Gly Gln Ile Phe Ala Leu Tyr Thr Gly Asn Ala Asn Asp Phe
    800                 805                 810

TCC CAA TTA CAA TGC AAA GCT GTA CCC GTA AAC TTA TCT GAC CCG CTT          628
Ser Gln Leu Gln Cys Lys Ala Val Pro Val Asn Leu Ser Asp Pro Leu
815                 820                 825                 830

CTT ATT GAG TGG GTC AAG TAT GAG GAT AAC CCA ATC CTG TAC ACT CCA          676
Leu Ile Glu Trp Val Lys Tyr Glu Asp Asn Pro Ile Leu Tyr Thr Pro
                835                 840                 845

CCA GGG ATT GGG TTA AAG GAC TAT CGG GAC CCG TCA ACA GTC TGG ACA          724
```

-continued

```
                Pro Gly Ile Gly Leu Lys Asp Tyr Arg Asp Pro Ser Thr Val Trp Thr
                                850                 855                 860

GGT CCC GAT GGA AAG CAT AGG ATG ATC ATG GGA ACT AAA CGT GGC AAT              772
Gly Pro Asp Gly Lys His Arg Met Ile Met Gly Thr Lys Arg Gly Asn
            865                 870                 875

ACA GGC ATG GTA CTT GTT TAC TAT ACC ACT GAT TAC ACG AAC TAC GAG              820
Thr Gly Met Val Leu Val Tyr Tyr Thr Thr Asp Tyr Thr Asn Tyr Glu
880                 885                 890

TTG TTG GAT GAG CCG TTG CAC TCT GTT CCC AAC ACC GAT ATG TGG GAA              868
Leu Leu Asp Glu Pro Leu His Ser Val Pro Asn Thr Asp Met Trp Glu
895                 900                 905                 910

TGC GTC GAC TTT TAC CCG GTT TCG TTA ACC AAT GAT AGT GCA CTT GAT              916
Cys Val Asp Phe Tyr Pro Val Ser Leu Thr Asn Asp Ser Ala Leu Asp
                915                 920                 925

ATG GCG GCC TAT GGG TCG GGT ATC AAA CAC GTT ATT AAA GAA AGT TGG              964
Met Ala Ala Tyr Gly Ser Gly Ile Lys His Val Ile Lys Glu Ser Trp
            930                 935                 940

GAG GGA CAT GGA ATG GAT TGG TAT TCA ATC GGG ACA TAT GAC GCG ATA             1012
Glu Gly His Gly Met Asp Trp Tyr Ser Ile Gly Thr Tyr Asp Ala Ile
            945                 950                 955

AAT GAT AAA TGG ACT CCC GAT AAC CCG GAA CTA GAT GTC GGT ATC GGG             1060
Asn Asp Lys Trp Thr Pro Asp Asn Pro Glu Leu Asp Val Gly Ile Gly
960                 965                 970

TTA CGG TGC GAT TAC GGG AGG TTT TTT GCA TCA AAG AGT CTT TAT GAC             1108
Leu Arg Cys Asp Tyr Gly Arg Phe Phe Ala Ser Lys Ser Leu Tyr Asp
975                 980                 985                 990

CCA TTG AAG AAA AGG AGG ATC ACT TGG GGT TAT GTT GGA GAA TCA GAT             1156
Pro Leu Lys Lys Arg Arg Ile Thr Trp Gly Tyr Val Gly Glu Ser Asp
                995                1000                1005

AGT GCT GAT CAG GAC CTC TCT AGA GGA TGG GCT ACT GTT TAT AAT GTT             1204
Ser Ala Asp Gln Asp Leu Ser Arg Gly Trp Ala Thr Val Tyr Asn Val
           1010                1015                1020

GGA AGA ACA ATT GTA CTA GAT AGA AAG ACC GGG ACC CAT TTA CTT CAT             1252
Gly Arg Thr Ile Val Leu Asp Arg Lys Thr Gly Thr His Leu Leu His
           1025                1030                1035

TGG CCC GTT GAG GAA GTC GAG AGT TTG AGA TAC AAC GGT CAG GAG TTT             1300
Trp Pro Val Glu Glu Val Glu Ser Leu Arg Tyr Asn Gly Gln Glu Phe
       1040                1045                1050

AAA GAG ATC AAG CTA GAG CCC GGT TCA ATC ATT CCA CTC GAC ATA GGC             1348
Lys Glu Ile Lys Leu Glu Pro Gly Ser Ile Ile Pro Leu Asp Ile Gly
1055                1060                1065                1070

ACG GCT ACA CAG TTG GAC ATA GTT GCA ACA TTT GAG GTG GAT CAA GCA             1396
Thr Ala Thr Gln Leu Asp Ile Val Ala Thr Phe Glu Val Asp Gln Ala
                1075                1080                1085

GCG TTG AAC GCG ACA AGT GAA ACC GAT GAT ATT TAT GGT TGC ACC ACT             1444
Ala Leu Asn Ala Thr Ser Glu Thr Asp Asp Ile Tyr Gly Cys Thr Thr
            1090                1095                1100

AGC TTA GGT GCA GCC CAA AGG GGA AGT TTG GGA CCA TTT GGT CTT GCG             1492
Ser Leu Gly Ala Ala Gln Arg Gly Ser Leu Gly Pro Phe Gly Leu Ala
           1105                1110                1115

GTT CTA GCC GAT GGA ACC CTT TCT GAG TTA ACT CCG GTT TAT TTC TAT             1540
Val Leu Ala Asp Gly Thr Leu Ser Glu Leu Thr Pro Val Tyr Phe Tyr
        1120                1125                1130

ATA GCT AAA AAG GCA GAT GGA GGT GTG TCG ACA CAT TTT TGT ACC GAT             1588
Ile Ala Lys Lys Ala Asp Gly Gly Val Ser Thr His Phe Cys Thr Asp
1135                1140                1145                1150

AAG CTA AGG TCA TCA CTA GAT TAT GAT GGG GAG AGA GTG GTG TAT GGG             1636
Lys Leu Arg Ser Ser Leu Asp Tyr Asp Gly Glu Arg Val Val Tyr Gly
                1155                1160                1165
```

-continued

```
GGC ACT GTT CCT GTG TTA GAT GAT GAA GAA CTC ACA ATG AGG CTA TTG      1684
Gly Thr Val Pro Val Leu Asp Asp Glu Glu Leu Thr Met Arg Leu Leu
            1170                1175                1180

GTG GAT CAT TCG ATA GTG GAG GGG TTT GCG CAA GGA GGA AGG ACG GTT      1732
Val Asp His Ser Ile Val Glu Gly Phe Ala Gln Gly Gly Arg Thr Val
        1185                1190                1195

ATA ACA TCA AGG GCG TAT CCA ACA AAA GCG ATA TAC GAA CAA GCG AAG      1780
Ile Thr Ser Arg Ala Tyr Pro Thr Lys Ala Ile Tyr Glu Gln Ala Lys
    1200                1205                1210

CTG TTC TTG TTC AAC AAC GCC ACA GGT ACG AGT GTG AAA GCA TCT CTC      1828
Leu Phe Leu Phe Asn Asn Ala Thr Gly Thr Ser Val Lys Ala Ser Leu
1215                1220                1225                1230

AAG ATT TGG CAA ATG GCT TCT GCA CCA ATT CAT CAA TAC CCT TTT          1873
Lys Ile Trp Gln Met Ala Ser Ala Pro Ile His Gln Tyr Pro Phe
                1235                1240                1245

TAATTACCGG CTATCGCTAT CCTTTTTGTT ATTGGTATTT ATGTATCTTA ATTTTCTTTT     1933

AAACCTTTTT ATTTGATAAA TATTAGTTCT TGTTATTGTG CTTCTAGTAA TAAATGAATG     1993

GTGTTATGGG                                                           2003
```

(2) INFORMATION FOR SEQ ID NO: 4:

(i) SEQUENCE CHARACTERISTICS:
      (A) LENGTH: 615 amino acids
      (B) TYPE: amino acid
      (D) TOPOLOGY: linear (ii) MOLECULE TYPE: protein (xi) SEQUENCE DESCRIPTION: SEQ ID NO: 4:

```
Met Gln Thr Pro Glu Pro Phe Thr Asp Leu Glu His Glu Pro His Thr
 1               5                  10                  15

Pro Leu Leu Asp His His Asn Pro Pro Gln Thr Thr Thr Lys
            20                  25                  30

Pro Leu Phe Thr Arg Val Val Ser Gly Val Thr Phe Val Leu Phe Phe
        35                  40                  45

Phe Gly Phe Ala Ile Val Phe Ile Val Leu Asn Gln Gln Asn Ser Ser
    50                  55                  60

Val Arg Ile Val Thr Asn Ser Glu Lys Ser Phe Ile Arg Tyr Ser Gln
65                  70                  75                  80

Thr Asp Arg Leu Ser Trp Glu Arg Thr Ala Phe His Phe Gln Pro Ala
                85                  90                  95

Lys Asn Phe Ile Tyr Asp Pro Asp Gly Gln Leu Phe His Met Gly Trp
            100                 105                 110

Tyr His Met Phe Tyr Gln Tyr Asn Pro Tyr Ala Pro Val Trp Gly Asn
        115                 120                 125

Met Ser Trp Gly His Ser Val Ser Lys Asp Met Ile Asn Trp Tyr Glu
    130                 135                 140

Leu Pro Val Ala Met Val Pro Thr Glu Trp Tyr Asp Ile Glu Gly Val
145                 150                 155                 160

Leu Ser Gly Ser Thr Thr Val Leu Pro Asn Gly Gln Ile Phe Ala Leu
                165                 170                 175

Tyr Thr Gly Asn Ala Asn Asp Phe Ser Gln Leu Gln Cys Lys Ala Val
            180                 185                 190

Pro Val Asn Leu Ser Asp Pro Leu Leu Ile Glu Trp Val Lys Tyr Glu
        195                 200                 205

Asp Asn Pro Ile Leu Tyr Thr Pro Pro Gly Ile Gly Leu Lys Asp Tyr
    210                 215                 220
```

-continued

Arg Asp Pro Ser Thr Val Trp Thr Gly Pro Asp Gly Lys His Arg Met
225                 230                 235                 240

Ile Met Gly Thr Lys Arg Gly Asn Thr Gly Met Val Leu Val Tyr Tyr
            245                 250                 255

Thr Thr Asp Tyr Thr Asn Tyr Glu Leu Leu Asp Glu Pro Leu His Ser
                260                 265                 270

Val Pro Asn Thr Asp Met Trp Glu Cys Val Asp Phe Tyr Pro Val Ser
        275                 280                 285

Leu Thr Asn Asp Ser Ala Leu Asp Met Ala Ala Tyr Gly Ser Gly Ile
    290                 295                 300

Lys His Val Ile Lys Glu Ser Trp Gly His Gly Met Asp Trp Tyr
305                 310                 315                 320

Ser Ile Gly Thr Tyr Asp Ala Ile Asn Asp Lys Trp Thr Pro Asp Asn
                325                 330                 335

Pro Glu Leu Asp Val Gly Ile Gly Leu Arg Cys Asp Tyr Gly Arg Phe
            340                 345                 350

Phe Ala Ser Lys Ser Leu Tyr Asp Pro Leu Lys Lys Arg Arg Ile Thr
        355                 360                 365

Trp Gly Tyr Val Gly Glu Ser Asp Ser Ala Asp Gln Asp Leu Ser Arg
    370                 375                 380

Gly Trp Ala Thr Val Tyr Asn Val Gly Arg Thr Ile Val Leu Asp Arg
385                 390                 395                 400

Lys Thr Gly Thr His Leu Leu His Trp Pro Val Glu Glu Val Glu Ser
                405                 410                 415

Leu Arg Tyr Asn Gly Gln Glu Phe Lys Glu Ile Lys Leu Glu Pro Gly
            420                 425                 430

Ser Ile Ile Pro Leu Asp Ile Gly Thr Ala Thr Gln Leu Asp Ile Val
        435                 440                 445

Ala Thr Phe Glu Val Asp Gln Ala Ala Leu Asn Ala Thr Ser Glu Thr
    450                 455                 460

Asp Asp Ile Tyr Gly Cys Thr Thr Ser Leu Gly Ala Ala Gln Arg Gly
465                 470                 475                 480

Ser Leu Gly Pro Phe Gly Leu Ala Val Leu Ala Asp Gly Thr Leu Ser
                485                 490                 495

Glu Leu Thr Pro Val Tyr Phe Tyr Ile Ala Lys Lys Ala Asp Gly Gly
            500                 505                 510

Val Ser Thr His Phe Cys Thr Asp Lys Leu Arg Ser Ser Leu Asp Tyr
        515                 520                 525

Asp Gly Glu Arg Val Val Tyr Gly Gly Thr Val Pro Val Leu Asp Asp
530                 535                 540

Glu Glu Leu Thr Met Arg Leu Leu Val Asp His Ser Ile Val Glu Gly
545                 550                 555                 560

Phe Ala Gln Gly Gly Arg Thr Val Ile Thr Ser Arg Ala Tyr Pro Thr
                565                 570                 575

Lys Ala Ile Tyr Glu Gln Ala Lys Leu Phe Leu Phe Asn Asn Ala Thr
            580                 585                 590

Gly Thr Ser Val Lys Ala Ser Leu Lys Ile Trp Gln Met Ala Ser Ala
        595                 600                 605

Pro Ile His Gln Tyr Pro Phe
    610                 615

(2) INFORMATION FOR SEQ ID NO: 5:

```
    (i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Helianthus tuberosus
        (B) STRAIN: Columbia
        (D) DEVELOPMENTAL STAGE: Adult
        (F) TISSUE TYPE: Tuber
        (G) CELL TYPE: storage parenchyma (vii) IMMEDIATE SOURCE:
        (A) LIBRARY: lambda Uni-Zap XR (Stratagene, USA)
        (B) CLONE: pSST103

(x) PUBLICATION INFORMATION:
        (H) DOCUMENT NUMBER: WO 89/12386 A1
        (I) FILING DATE: 21-JUN-1989
        (J) PUBLICATION DATE: 28-DEC-1989
        (K) RELEVANT RESIDUES IN SEQ ID NO: 5: FROM 1 TO 4100

(x) PUBLICATION INFORMATION:
        (H) DOCUMENT NUMBER: WO 94/04692 A1
        (I) FILING DATE: 09-AUG-1993
        (J) PUBLICATION DATE: 03-MAR-1994
        (K) RELEVANT RESIDUES IN SEQ ID NO: 5: FROM 1 TO 1438

(x) PUBLICATION INFORMATION:
        (H) DOCUMENT NUMBER: WO 94/14970 A1
        (I) FILING DATE: 28-DEC-1993
        (J) PUBLICATION DATE: 07-JUL-1994

(xi) SEQUENCE DESCRIPTION: SEQ ID NO: 5:

GARCARYTNC CNGTNTAYTT YTAYATHGCN AAR                                      33

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Helianthus tuberosus
        (B) STRAIN: Columbia
        (D) DEVELOPMENTAL STAGE: Adult
        (F) TISSUE TYPE: Tuber
        (G) CELL TYPE: storage parenchyma (vii) IMMEDIATE SOURCE:
        (A) LIBRARY: lambda Uni-Zap XR (Stratagene, USA)
        (B) CLONE: pFFT111

(x) PUBLICATION INFORMATION:
        (H) DOCUMENT NUMBER: WO 89/12386 A1
        (I) FILING DATE: 21-JUN-1989
        (J) PUBLICATION DATE: 28-DEC-1989
        (K) RELEVANT RESIDUES IN SEQ ID NO: 6: FROM 1 TO 4100

(x) PUBLICATION INFORMATION:
        (H) DOCUMENT NUMBER: WO 94/04692 A1
        (I) FILING DATE: 09-AUG-1993
```

(J) PUBLICATION DATE: 03-MAR-1994
            (K) RELEVANT RESIDUES IN SEQ ID NO: 6: FROM 1 TO 1438

(x) PUBLICATION INFORMATION:
            (H) DOCUMENT NUMBER: WO 94/14970 A1
            (I) FILING DATE: 28-DEC-1993
            (J) PUBLICATION DATE: 07-JUL-1994

(xi) SEQUENCE DESCRIPTION: SEQ ID NO: 6:

GGNTGGGCNA CNGTNTAYAA Y                                              21

(2) INFORMATION FOR SEQ ID NO: 7:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Helianthus tuberosus
            (B) STRAIN: Columbia
            (D) DEVELOPMENTAL STAGE: Adult
            (F) TISSUE TYPE: Tuber
            (G) CELL TYPE: storage parenchyma (vii) IMMEDIATE SOURCE:
            (A) LIBRARY: lambda Uni-Zap XR (Stratagene, USA)
            (B) CLONE: pFFT111

(x) PUBLICATION INFORMATION:
            (H) DOCUMENT NUMBER: WO 89/12386 A1
            (I) FILING DATE: 21-JUN-1989
            (J) PUBLICATION DATE: 28-DEC-1989
            (K) RELEVANT RESIDUES IN SEQ ID NO: 7: FROM 1 TO 4100

(x) PUBLICATION INFORMATION:
            (H) DOCUMENT NUMBER: WO 94/04692 A1
            (I) FILING DATE: 09-AUG-1993
            (J) PUBLICATION DATE: 03-MAR-1994
            (K) RELEVANT RESIDUES IN SEQ ID NO: 7: FROM 1 TO 1438

(x) PUBLICATION INFORMATION:
            (H) DOCUMENT NUMBER: WO 94/14970 A1
            (I) FILING DATE: 28-DEC-1993
            (J) PUBLICATION DATE: 07-JUL-1994

(xi) SEQUENCE DESCRIPTION: SEQ ID NO: 7:

ATHGTNGARG GNTTYGCNCA R                                              21

(2) INFORMATION FOR SEQ ID NO: 8:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Helianthus tuberosus
            (B) STRAIN: Columbia
            (D) DEVELOPMENTAL STAGE: Adult
            (F) TISSUE TYPE: Tuber

```
            (G) CELL TYPE: storage parenchyma (vii) IMMEDIATE SOURCE:
            (A) LIBRARY: lambda Uni-Zap XR (Stratagene, USA)
            (B) CLONE: pFFT111

(x) PUBLICATION INFORMATION:
            (H) DOCUMENT NUMBER: WO 89/12386 A1
            (I) FILING DATE: 21-JUN-1989
            (J) PUBLICATION DATE: 28-DEC-1989
            (K) RELEVANT RESIDUES IN SEQ ID NO: 8: FROM 1 TO 4100

(x) PUBLICATION INFORMATION:
            (H) DOCUMENT NUMBER: WO 94/04692 A1
            (I) FILING DATE: 09-AUG-1993
            (J) PUBLICATION DATE: 03-MAR-1994
            (K) RELEVANT RESIDUES IN SEQ ID NO: 8: FROM 1 TO 1438

(x) PUBLICATION INFORMATION:
            (H) DOCUMENT NUMBER: WO 94/14970 A1
            (I) FILING DATE: 28-DEC-1993
            (J) PUBLICATION DATE: 07-JUL-1994

(xi) SEQUENCE DESCRIPTION: SEQ ID NO: 8:

CCGAATTCAA TACGACTCAC TATAGCG                                             27

(2) INFORMATION FOR SEQ ID NO: 9:

(i) SEQUENCE CHARACTERISTICS:
            (A) LENGTH: 16 amino acids
            (B) TYPE: amino acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Helianthus tuberosus
            (B) STRAIN: Columbia
            (D) DEVELOPMENTAL STAGE: Adult
            (F) TISSUE TYPE: Tuber
            (G) CELL TYPE: storage parenchyma (vii) IMMEDIATE SOURCE:
            (A) LIBRARY: lambda Uni-Zap XR (Stratagene, USA)
            (B) CLONE: pSST103

(x) PUBLICATION INFORMATION:
            (H) DOCUMENT NUMBER: WO 89/12386 A1
            (I) FILING DATE: 21-JUN-1989
            (J) PUBLICATION DATE: 28-DEC-1989
            (K) RELEVANT RESIDUES IN SEQ ID NO: 9: FROM 1 TO 4100

(x) PUBLICATION INFORMATION:
            (H) DOCUMENT NUMBER: WO 94/04692 A1
            (I) FILING DATE: 09-AUG-1993
            (J) PUBLICATION DATE: 03-MAR-1994
            (K) RELEVANT RESIDUES IN SEQ ID NO: 9: FROM 1 TO 1438

(x) PUBLICATION INFORMATION:
            (H) DOCUMENT NUMBER: WO 94/14970 A1
            (I) FILING DATE: 28-DEC-1993
            (J) PUBLICATION DATE: 07-JUL-1994

(xi) SEQUENCE DESCRIPTION: SEQ ID NO: 9:

Ala Asp Val Leu Phe Xaa Xaa Thr Thr Ser Glu Gly Ser Val Ala Arg
  1               5                  10                  15

(2) INFORMATION FOR SEQ ID NO: 10:

(i) SEQUENCE CHARACTERISTICS:
```

(A) LENGTH: 11 amino acids
            (B) TYPE: amino acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Helianthus tuberosus
            (B) STRAIN: Columbia
            (D) DEVELOPMENTAL STAGE: Adult
            (F) TISSUE TYPE: Tuber
            (G) CELL TYPE: storage parenchyma (vii) IMMEDIATE SOURCE:
            (A) LIBRARY: lambda Uni-Zap XR (Stratagene, USA)
            (B) CLONE: pSST103

(x) PUBLICATION INFORMATION:
            (H) DOCUMENT NUMBER: WO 89/12386 A1
            (I) FILING DATE: 21-JUN-1989
            (J) PUBLICATION DATE: 28-DEC-1989
            (K) RELEVANT RESIDUES IN SEQ ID NO: 10: FROM 1 TO 4100

(x) PUBLICATION INFORMATION:
            (H) DOCUMENT NUMBER: WO 94/04692 A1
            (I) FILING DATE: 09-AUG-1993
            (J) PUBLICATION DATE: 03-MAR-1994
            (K) RELEVANT RESIDUES IN SEQ ID NO: 10: FROM 1 TO 1438

(x) PUBLICATION INFORMATION:
            (H) DOCUMENT NUMBER: WO 94/14970 A1
            (I) FILING DATE: 28-DEC-1993
            (J) PUBLICATION DATE: 07-JUL-1994

(xi) SEQUENCE DESCRIPTION: SEQ ID NO: 10:

Glu Gln Leu Pro Val Tyr Phe Tyr Ile Ala Lys
1               5                   10

(2) INFORMATION FOR SEQ ID NO: 11:

(i) SEQUENCE CHARACTERISTICS:
            (A) LENGTH: 8 amino acids
            (B) TYPE: amino acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Helianthus tuberosus
            (B) STRAIN: Columbia
            (D) DEVELOPMENTAL STAGE: Adult
            (F) TISSUE TYPE: Tuber
            (G) CELL TYPE: storage parenchyma (vii) IMMEDIATE SOURCE:
            (A) LIBRARY: lambda Uni-Zap XR (Stratagene, USA)
            (B) CLONE: pFFT111

(x) PUBLICATION INFORMATION:
            (H) DOCUMENT NUMBER: WO 89/12386 A1
            (I) FILING DATE: 21-JUN-1989
            (J) PUBLICATION DATE: 28-DEC-1989
            (K) RELEVANT RESIDUES IN SEQ ID NO: 11: FROM 1 TO 4100

(x) PUBLICATION INFORMATION:
            (H) DOCUMENT NUMBER: WO 94/04692 A1
            (I) FILING DATE: 09-AUG-1993

```
            (J) PUBLICATION DATE: 03-MAR-1994
            (K) RELEVANT RESIDUES IN SEQ ID NO: 11: FROM 1 TO 1438

(x) PUBLICATION INFORMATION:
            (H) DOCUMENT NUMBER: WO 94/14970 A1
            (I) FILING DATE: 28-DEC-1993
            (J) PUBLICATION DATE: 07-JUL-1994

(xi) SEQUENCE DESCRIPTION: SEQ ID NO: 11:

Val Val Leu Asp Leu Glu Thr Lys
 1               5

(2) INFORMATION FOR SEQ ID NO: 12:

(i) SEQUENCE CHARACTERISTICS:
            (A) LENGTH: 15 amino acids
            (B) TYPE: amino acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Helianthus tuberosus
            (B) STRAIN: Columbia
            (D) DEVELOPMENTAL STAGE: Adult
            (F) TISSUE TYPE: Tuber
            (G) CELL TYPE: storage parenchyma (vii) IMMEDIATE SOURCE:
            (A) LIBRARY: lambda Uni-Zap XR (Stratagene, USA)
            (B) CLONE: pSST103

(x) PUBLICATION INFORMATION:
            (H) DOCUMENT NUMBER: WO 89/12386 A1
            (I) FILING DATE: 21-JUN-1989
            (J) PUBLICATION DATE: 28-DEC-1989
            (K) RELEVANT RESIDUES IN SEQ ID NO: 12: FROM 1 TO 4100

(x) PUBLICATION INFORMATION:
            (H) DOCUMENT NUMBER: WO 94/04692 A1
            (I) FILING DATE: 09-AUG-1993
            (J) PUBLICATION DATE: 03-MAR-1994
            (K) RELEVANT RESIDUES IN SEQ ID NO: 12: FROM 1 TO 1438

(x) PUBLICATION INFORMATION:
            (H) DOCUMENT NUMBER: WO 94/14970 A1
            (I) FILING DATE: 28-DEC-1993
            (J) PUBLICATION DATE: 07-JUL-1994

(xi) SEQUENCE DESCRIPTION: SEQ ID NO: 12:

Phe Arg Asp Pro Ser Thr Leu Trp Leu Xaa Pro Asp Gly Glu Tyr
 1               5                  10                  15

(2) INFORMATION FOR SEQ ID NO: 13:

(i) SEQUENCE CHARACTERISTICS:
            (A) LENGTH: 6 amino acids
            (B) TYPE: amino acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Helianthus tuberosus
            (B) STRAIN: Columbia
```

```
            (D) DEVELOPMENTAL STAGE: Adult
            (F) TISSUE TYPE: Tuber
            (G) CELL TYPE: storage parenchyma (vii) IMMEDIATE SOURCE:
            (A) LIBRARY: lambda Uni-Zap XR (Stratagene, USA)
            (B) CLONE: pSST103

(x) PUBLICATION INFORMATION:
            (H) DOCUMENT NUMBER: WO 89/12386 A1
            (I) FILING DATE: 21-JUN-1989
            (J) PUBLICATION DATE: 28-DEC-1989
            (K) RELEVANT RESIDUES IN SEQ ID NO: 13: FROM 1 TO 4100

(x) PUBLICATION INFORMATION:
            (H) DOCUMENT NUMBER: WO 94/04692 A1
            (I) FILING DATE: 09-AUG-1993
            (J) PUBLICATION DATE: 03-MAR-1994
            (K) RELEVANT RESIDUES IN SEQ ID NO: 13: FROM 1 TO 1438

(x) PUBLICATION INFORMATION:
            (H) DOCUMENT NUMBER: WO 94/14970 A1
            (I) FILING DATE: 28-DEC-1993
            (J) PUBLICATION DATE: 07-JUL-1994

(xi) SEQUENCE DESCRIPTION: SEQ ID NO: 13:

Gly Trp Ala Asn Ile Leu
1               5

(2) INFORMATION FOR SEQ ID NO: 14:

(i) SEQUENCE CHARACTERISTICS:
            (A) LENGTH: 10 amino acids
            (B) TYPE: amino acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Helianthus tuberosus
            (B) STRAIN: Columbia
            (D) DEVELOPMENTAL STAGE: Adult
            (F) TISSUE TYPE: Tuber
            (G) CELL TYPE: storage parenchyma (vii) IMMEDIATE SOURCE:
            (A) LIBRARY: lambda Uni-Zap XR (Stratagene, USA)
            (B) CLONE: pFFT111

(x) PUBLICATION INFORMATION:
            (H) DOCUMENT NUMBER: WO 89/12386 A1
            (I) FILING DATE: 21-JUN-1989
            (J) PUBLICATION DATE: 28-DEC-1989
            (K) RELEVANT RESIDUES IN SEQ ID NO: 14: FROM 1 TO 4100

(x) PUBLICATION INFORMATION:
            (H) DOCUMENT NUMBER: WO 94/04692 A1
            (I) FILING DATE: 09-AUG-1993
            (J) PUBLICATION DATE: 03-MAR-1994
            (K) RELEVANT RESIDUES IN SEQ ID NO: 14: FROM 1 TO 1438

(x) PUBLICATION INFORMATION:
            (H) DOCUMENT NUMBER: WO 94/14970 A1
            (I) FILING DATE: 28-DEC-1993
            (J) PUBLICATION DATE: 07-JUL-1994

(xi) SEQUENCE DESCRIPTION: SEQ ID NO: 14:

Gly Trp Ala Thr Val Tyr Asn Val Gly Arg
1               5                   10
```

```
(2) INFORMATION FOR SEQ ID NO: 15:

(i) SEQUENCE CHARACTERISTICS:
        (A) LENGTH: 16 amino acids
        (B) TYPE: amino acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Helianthus tuberosus
        (B) STRAIN: Columbia
        (D) DEVELOPMENTAL STAGE: Adult
        (F) TISSUE TYPE: Tuber
        (G) CELL TYPE: storage parenchyma (vii) IMMEDIATE SOURCE:
        (A) LIBRARY: lambda Uni-Zap XR (Stratagene, USA)
        (B) CLONE: pFFT111

(x) PUBLICATION INFORMATION:
        (H) DOCUMENT NUMBER: WO 89/12386 A1
        (I) FILING DATE: 21-JUN-1989
        (J) PUBLICATION DATE: 28-DEC-1989
        (K) RELEVANT RESIDUES IN SEQ ID NO: 15: FROM 1 TO 4100

(x) PUBLICATION INFORMATION:
        (H) DOCUMENT NUMBER: WO 94/04692 A1
        (I) FILING DATE: 09-AUG-1993
        (J) PUBLICATION DATE: 03-MAR-1994
        (K) RELEVANT RESIDUES IN SEQ ID NO: 15: FROM 1 TO 1438

(x) PUBLICATION INFORMATION:
        (H) DOCUMENT NUMBER: WO 94/14970 A1
        (I) FILING DATE: 28-DEC-1993
        (J) PUBLICATION DATE: 07-JUL-1994

(xi) SEQUENCE DESCRIPTION: SEQ ID NO: 15:

Leu Leu Val Asp His Ser Ile Val Glu Gly Phe Ala Gln Gly Gly Arg
1               5                   10                  15

(2) INFORMATION FOR SEQ ID NO: 16:

(i) SEQUENCE CHARACTERISTICS:
        (A) LENGTH: 6 amino acids
        (B) TYPE: amino acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Helianthus tuberosus
        (B) STRAIN: Columbia
        (D) DEVELOPMENTAL STAGE: Adult
        (F) TISSUE TYPE: Tuber
        (G) CELL TYPE: storage parenchyma (vii) IMMEDIATE SOURCE:
        (A) LIBRARY: lambda Uni-Zap XR (Stratagene, USA)
        (B) CLONE: pFFT111

(x) PUBLICATION INFORMATION:
        (H) DOCUMENT NUMBER: WO 89/12386 A1
        (I) FILING DATE: 21-JUN-1989
        (J) PUBLICATION DATE: 28-DEC-1989
        (K) RELEVANT RESIDUES IN SEQ ID NO: 16: FROM 1 TO 4100
```

```
            -continued (x) PUBLICATION INFORMATION:
       (H) DOCUMENT NUMBER: WO 94/04692 A1
       (I) FILING DATE: 09-AUG-1993
       (J) PUBLICATION DATE: 03-MAR-1994
       (K) RELEVANT RESIDUES IN SEQ ID NO: 16: FROM 1 TO 1438

(x) PUBLICATION INFORMATION:
       (H) DOCUMENT NUMBER: WO 94/14970 A1
       (I) FILING DATE: 28-DEC-1993
       (J) PUBLICATION DATE: 07-JUL-1994

(xi) SEQUENCE DESCRIPTION: SEQ ID NO: 16:

Val Gly Glu Ser Asp Ser
1               5
```